United States Patent
Frey et al.

(10) Patent No.: US 12,402,931 B2
(45) Date of Patent: Sep. 2, 2025

(54) ELECTROSURGICAL DEVICE WITH ILLUMINATION AND SMOKE EVACUATION FEATURES

(71) Applicant: Stryker European Operations Limited, Cork (IE)

(72) Inventors: Laura Constance Frey, Belfast (IE); Conor Mac An Tuile, Muine Bheag (IE); Scott McFarland, Greenisland (IE); Paul Sheridan, Wexford (IE); Micheal Burke, Cork (IE)

(73) Assignee: Stryker European Operations Limited, Carringtwohill (IE)

( * ) Notice: Subject to any disclaimer, the term of this patent is extended or adjusted under 35 U.S.C. 154(b) by 467 days.

(21) Appl. No.: 17/619,518

(22) PCT Filed: Nov. 12, 2020

(86) PCT No.: PCT/IB2020/000946
§ 371 (c)(1),
(2) Date: Dec. 15, 2021

(87) PCT Pub. No.: WO2021/094829
PCT Pub. Date: May 20, 2021

(65) Prior Publication Data
US 2022/0304741 A1    Sep. 29, 2022

Related U.S. Application Data

(60) Provisional application No. 62/934,512, filed on Nov. 12, 2019, provisional application No. 62/976,744, filed on Feb. 14, 2020.

(51) Int. Cl.
*A61B 18/14*     (2006.01)
*A61B 90/30*     (2016.01)
(Continued)

(52) U.S. Cl.
CPC .......... *A61B 18/1402* (2013.01); *A61B 90/30* (2016.02); *A61B 2017/00991* (2013.01);
(Continued)

(58) Field of Classification Search
CPC ................ A61B 18/1402; A61B 90/30; A61B 2090/306; A61B 2090/309; A61B 2218/007; A61B 2218/008
See application file for complete search history.

(56) References Cited

U.S. PATENT DOCUMENTS

| | | |
|---|---|---|
| 11,547,463 B2 | 1/2023 | Manley et al. |
| 2002/0103485 A1 | 8/2002 | Melnyk et al. |

(Continued)

FOREIGN PATENT DOCUMENTS

| | | |
|---|---|---|
| CN | 1929794 A | 3/2007 |
| CN | 201510348 A | 6/2010 |

(Continued)

OTHER PUBLICATIONS

International Search Report mailed on May 11, 2021, issued in connection with International Application No. PCTIB2020000946, filed on Nov. 12, 2020, 6 pages.

(Continued)

*Primary Examiner* — Sean W Collins
(74) *Attorney, Agent, or Firm* — McDonnell Boehnen Hulbert & Berghoff LLP

(57) ABSTRACT

In an example, an electrosurgical device includes a housing defining an interior bore. The electrosurgical device also includes a shaft telescopically moveable in the interior bore of the housing. The shaft includes an optical waveguide at a distal end of the shaft, and a smoke evacuation channel circumferentially surrounding the optical waveguide at the distal end of the shaft. The electrosurgical device also includes an electrosurgical electrode coupled to the shaft.

20 Claims, 14 Drawing Sheets

(51) Int. Cl.
*A61B 17/00* (2006.01)
*A61B 18/00* (2006.01)

(52) U.S. Cl.
CPC .............. *A61B 2018/00702* (2013.01); *A61B 2090/306* (2016.02); *A61B 2090/309* (2016.02); *A61B 2218/008* (2013.01)

(56) References Cited

U.S. PATENT DOCUMENTS

| | | | |
|---|---|---|---|
| 2012/0283728 A1* | 11/2012 | Cosmescu | A61B 18/1477 |
| | | | 606/45 |
| 2014/0257273 A1 | 9/2014 | Cosmescu | |
| 2015/0209100 A1* | 7/2015 | Ineson | A61B 18/1402 |
| | | | 606/42 |
| 2016/0157920 A1 | 6/2016 | Vayser et al. | |
| 2017/0290628 A1 | 10/2017 | Pepe et al. | |
| 2018/0078301 A1* | 3/2018 | Vayser | A61B 18/1402 |
| 2018/0333201 A1 | 11/2018 | Greep et al. | |
| 2019/0090975 A1* | 3/2019 | Hernandez | A61B 18/1402 |

FOREIGN PATENT DOCUMENTS

| | | |
|---|---|---|
| CN | 106999716 A | 8/2017 |
| CN | 107847268 A | 3/2018 |
| CN | 209490088 U | 10/2019 |
| JP | 2016-508847 A | 3/2016 |
| JP | 2016-512736 A | 5/2016 |
| JP | 2018-501848 A | 1/2018 |
| JP | 2018-524078 A | 8/2018 |
| JP | 2019-528897 A | 10/2019 |
| WO | 2016/094443 A1 | 6/2016 |

OTHER PUBLICATIONS

Written Opinion mailed on May 11, 2021, issued in connection with International Application No. PCTIB2020000946, filed on Nov. 12, 2020, 9 pages.
Office Action issued by the Japanese Patent Office in Application No. 2021-576412 dated Jul. 5, 2024. English translation included.
First Office Action issued by the Chinese Patent Office in Application No. 202080044946.1 dated Oct. 25, 2024. English translation included.

* cited by examiner

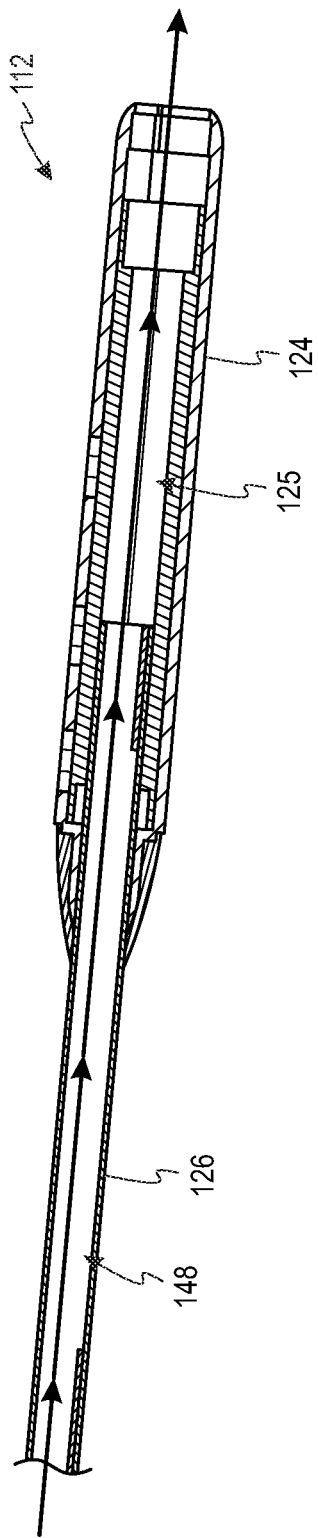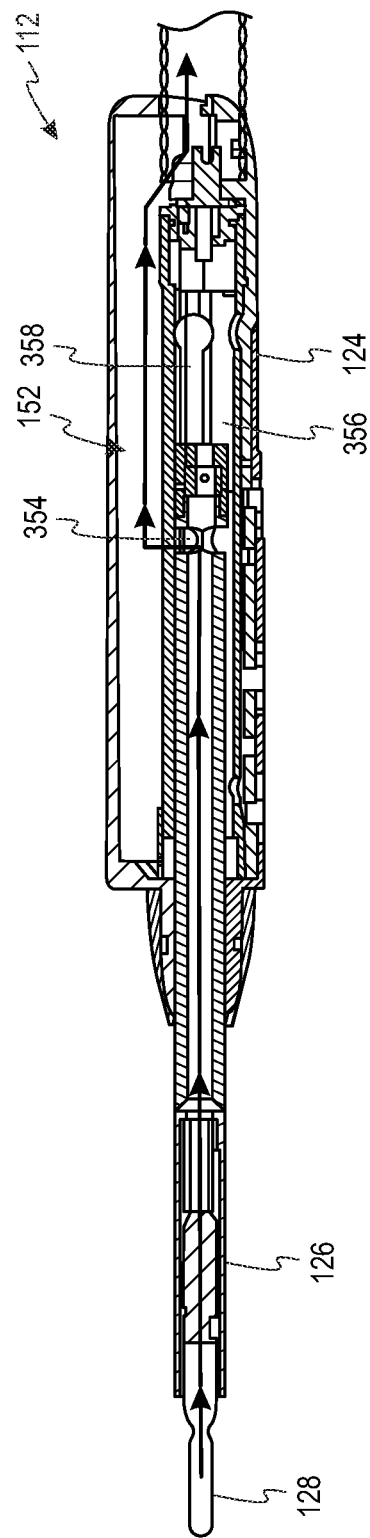

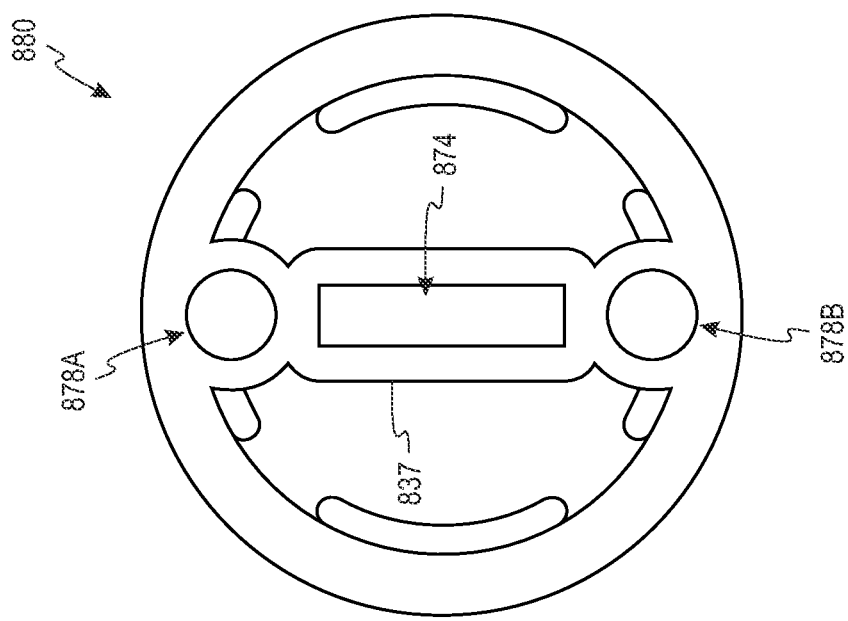
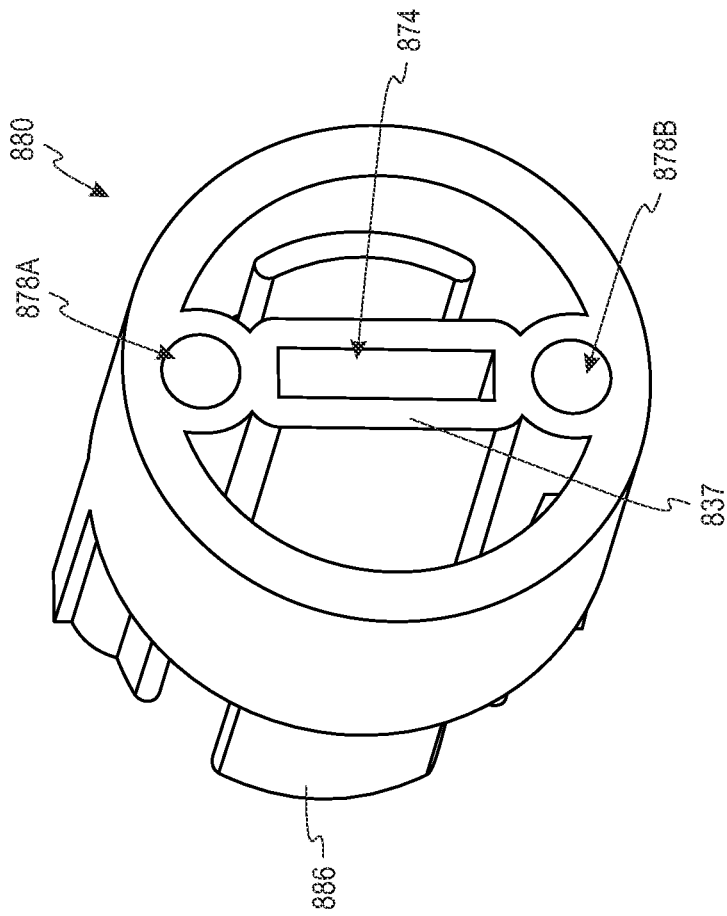

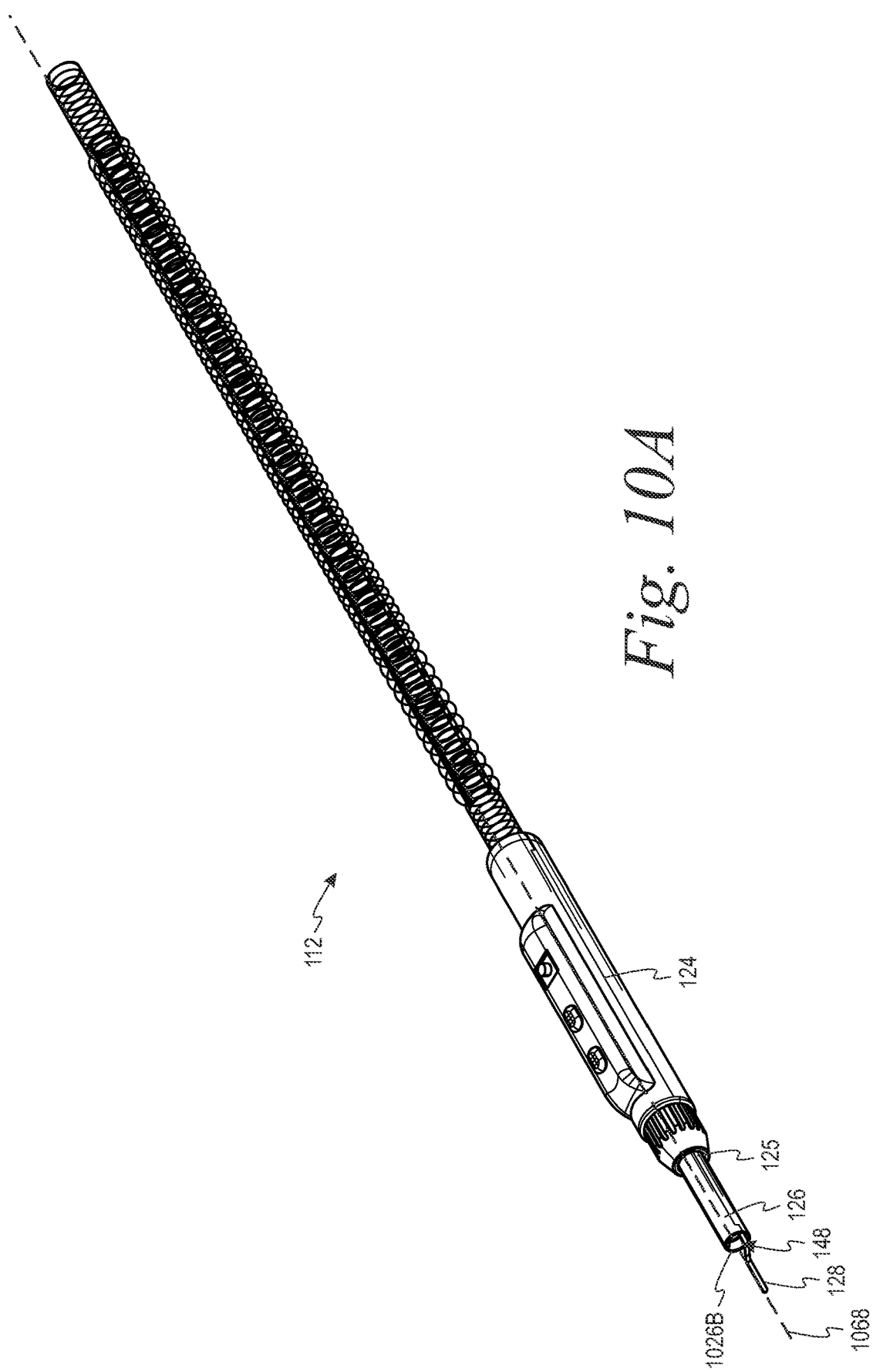

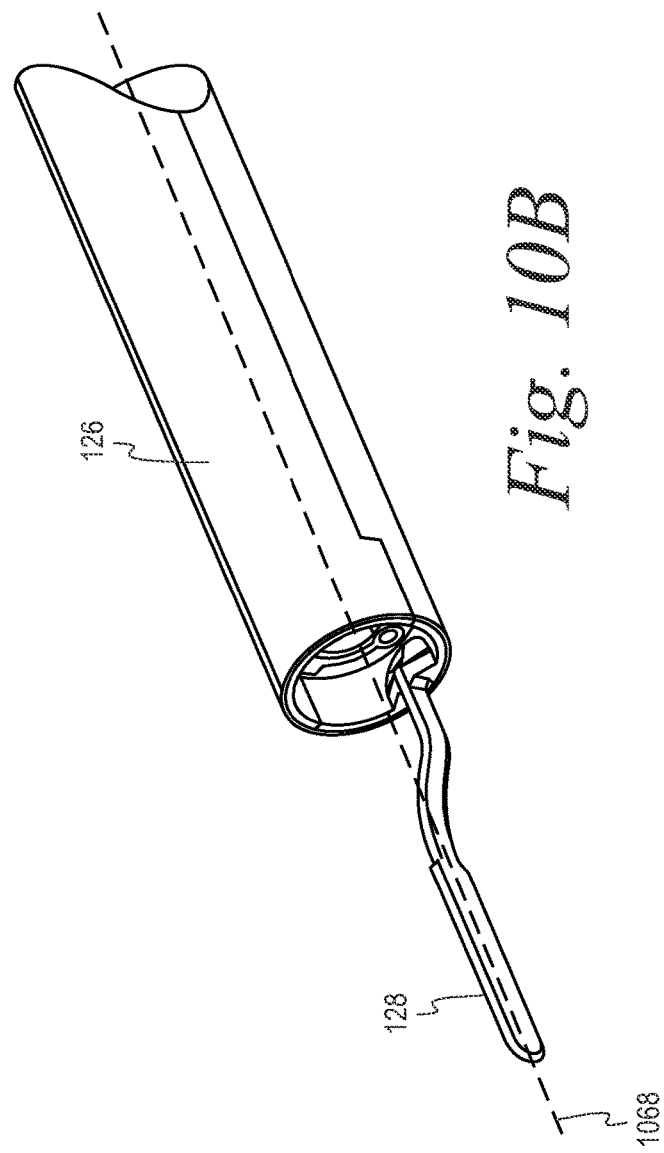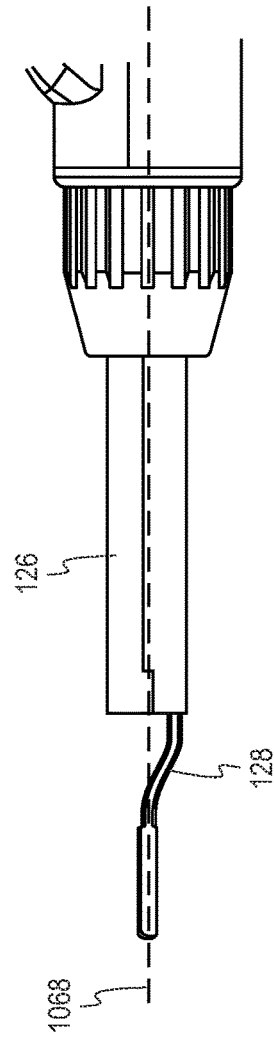

ELECTROSURGICAL DEVICE WITH ILLUMINATION AND SMOKE EVACUATION FEATURES

CROSS-REFERENCE TO RELATED APPLICATIONS

This application is a U.S. national phase of International Application No. PCT/IB2020/000946, filed on Nov. 12, 2020, which claims the benefit of U.S. Provisional Patent Application No. 62/976,744, filed on Feb. 14, 2020, and U.S. Provisional Patent Application No. 62/934,512 filed on Nov. 12, 2019, the contents of which are hereby incorporated by reference in their entirety.

FIELD

The present disclosure generally relates to methods and apparatus for conveying electrical energy and, more specifically, to electrosurgical devices and the methods providing for telescopic adjustment of an electrosurgical electrode.

BACKGROUND

Electrosurgery involves applying a radio frequency (RF) electric current (also referred to as electrosurgical energy) to biological tissue to cut, coagulate, or modify the biological tissue during an electrosurgical procedure. Specifically, an electrosurgical generator generates and provides the electric current to an active electrode, which applies the electric current (and, thus, electrical power) to the tissue. The electric current passes through the tissue and returns to the generator via a return electrode (also referred to as a "dispersive electrode"). As the electric current passes through the tissue, an impedance of the tissue converts a portion of the electric current into thermal energy (e.g., via the principles of resistive heating), which increases a temperature of the tissue and induces modifications to the tissue (e.g., cutting, coagulating, ablating, and/or sealing the tissue).

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 2 depicts a cross-sectional view of an electrosurgical device, according to an example.

FIG. 3 depicts a cross-sectional view of an electrosurgical device, according to an example.

FIG. 8A depicts a perspective view of a distal end portion of a shaft of an electrosurgical device, according to example.

FIG. 8B depicts a side view of the distal end portion shown in FIG. 8A, according to example.

FIG. 10A depicts a perspective view of an electrosurgical device 112, according to another example.

FIG. 10B depicts a perspective view of a distal end of a shaft of the electrosurgical device shown in FIG. 10A, according to an example.

FIG. 10C depicts a side view of a distal end of the shaft of the electrosurgical device shown in FIG. 10B, according to an example.

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As noted above, an electrosurgical device can use electrical energy supplied by an electrosurgical generator to apply electrosurgical energy from an electrosurgical electrode to a tissue. As such, the electrosurgical device generally includes a housing in which one or more conductors are disposed for supplying the electrosurgical energy to the electrosurgical electrode. Some electrosurgical devices include a shaft that is telescopically adjustable relative to the housing. This can facilitate adjusting a length of the electrosurgical device to treat differently sized and/or shaped target tissues.

Figure 1:
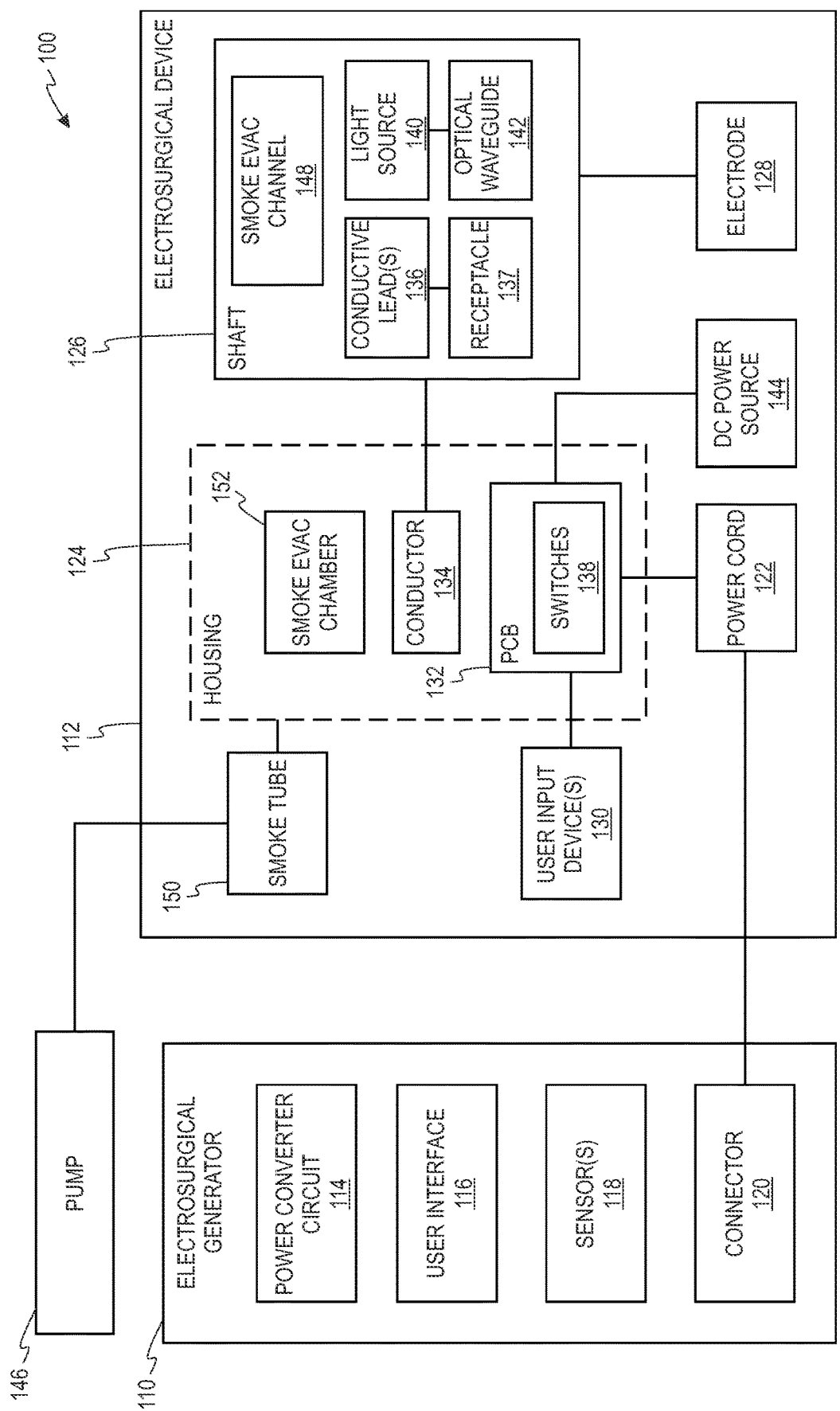
FIG. 1 depicts a simplified block diagram of an electrosurgical system, according to an example.

Referring now to FIG. 1, an electrosurgical system 100 is shown according to an example. As shown in FIG. 1, the electrosurgical system 100 includes an electrosurgical generator 110 and an electrosurgical device 112. In general, the electrosurgical generator 110 can generate electrosurgical energy that is suitable for performing electrosurgery on a patient. For instance, the electrosurgical generator 110 can include a power converter circuit 114 that can convert a grid power to electrosurgical energy such as, for example, a radio frequency (RF) output power. As an example, the power converter circuit 114 can include one or more electrical components (e.g., one or more transformers) that can control a voltage, a current, and/or a frequency of the electrosurgical energy.

Within examples, the electrosurgical generator 110 can include a user interface 116 that can receive one or more inputs from a user and/or provide one or more outputs to the user. As examples, the user interface 116 can include one or more buttons, one or more switches, one or more dials, one or more keypads, one or more touchscreens, and/or one or more display screens.

In an example, the user interface 116 can be operable to select a mode of operation from among a plurality of modes of operation for the electrosurgical generator 110. As examples, the modes of operation can include a cutting mode, a coagulating mode, an ablating mode, and/or a sealing mode. Combinations of these waveforms can also be formed to create blended modes. In one implementation, the modes of operation can correspond to respective waveforms for the electrosurgical energy. As such, in this implementation, the electrosurgical generator 110 can generate the electrosurgical energy with a waveform selected from a plurality of waveforms based, at least in part, on the mode of operation selected using the user interface 116.

The electrosurgical generator 110 can also include one or more sensors 118 that can sense one or more conditions related to the electrosurgical energy and/or the target tissue. As examples, the sensor(s) 118 can include one or more current sensors, one or more voltage sensors, one or more temperature sensors, and/or one or more bioimpedance sensors. Within examples, the electrosurgical generator 110 can additionally or alternatively generate the electrosurgical energy with an amount of electrosurgical energy (e.g., an electrical power) and/or a waveform selected from among the plurality of waveforms based on one or more parameters related to the condition(s) sensed by the sensor(s) 118.

In one example, the electrosurgical energy can have a frequency that is greater than approximately 100 kilohertz (kHz) to reduce (or avoid) stimulating a muscle and/or a nerve near the target tissue. In another example, the electrosurgical energy can have a frequency that is between approximately 300 kHz and approximately 500 kHz.

In FIG. 1, the electrosurgical generator 110 also includes a connector 120 that can facilitate coupling the electrosurgical generator 110 to the electrosurgical device 112. For example, the electrosurgical device 112 can include a power cord 122 having a plug, which can be coupled to a socket of the connector 120 of the electrosurgical generator 110. In this arrangement, the electrosurgical generator 110 can supply the electrosurgical energy to the electrosurgical device 112 via the coupling between the connector 120 of the electrosurgical generator 110 and the power cord 122 of the electrosurgical device 112.

As shown in FIG. 1, the electrosurgical device 112 can include a housing 124 defining an interior bore 125, a shaft 126 extending in a distal direction from the housing 124, and an electrosurgical electrode 128 coupled to the shaft 126. In general, the housing 124 can be configured to facilitate a user gripping and manipulating the electrosurgical device 112 while performing electrosurgery. For example, the housing 124 can have a shape and/or a size that can facilitate a user performing electrosurgery by manipulating the electrosurgical device 112 using a single hand. In one implementation, the housing 124 can have a shape and/or a size that facilitates the user holding the electrosurgical device 112 in a writing utensil gripping manner (e.g., the electro surgical device 112 can be an electrosurgical pencil).

Additionally, for example, the housing 124 can be constructed from one or more materials that are electrical insulators (e.g., a plastic material). This can facilitate insulating the user from the electrosurgical energy flowing through the electrosurgical device 112 while performing the electrosurgery.

In some implementations, the shaft 126 can be fixedly coupled to the housing 124. In other implementations, the shaft 126 can be telescopically moveable relative to the housing 124. For example, the shaft 126 can be telescopically moveable in an interior bore defined by the housing 124 to extend the shaft 126 in the distal direction and retract the shaft 126 in a proximal direction relative to the housing 124 (e.g., movable along a longitudinal axis of the electrosurgical device 112). As noted above, the electrosurgical electrode 128 is coupled to the shaft 126 and, thus, the electrosurgical electrode 128 moves together with the shaft 126 relative to the housing 124. This can provide for adjusting a length of the electrosurgical device 112, which can facilitate performing electrosurgery at a plurality of different depths within tissue (e.g., due to different anatomical shapes and/or sizes of patients) and/or at a plurality of different angles.

In some examples, the shaft 126 can additionally or alternatively be rotatable about an axis of rotation that is parallel to the longitudinal axis of the electrosurgical device 112. In another example, the electrosurgical electrode 128 can be additionally or alternatively rotatable relative to the shaft 126. Rotating the shaft 126 and/or the electrosurgical electrode 128 relative to the housing 124 can facilitate adjusting an angle of the electrosurgical electrode 128 relative to one or more user input device(s) 130 of the electrosurgical device 112. In this arrangement, a user can comfortably grip the housing 124 in a position in which their fingers can comfortably operate the user input device(s) 130 while the electrosurgical electrode 128 is set at a rotational position selected from among a plurality of rotational positions relative to the housing 124 based on, for example, a location, a size, and/or a shape of a surgical site in which the user is operating.

The user input device(s) 130 can select between the modes of operation of the electrosurgical device 112 and/or the electrosurgical generator 110. For instance, in one implementation, the user input device(s) 130 can be configured to select between a cutting mode of operation and a coagulation mode of operation. Responsive to actuation of the user input device(s) 130 of the electrosurgical device 112, the electrosurgical device 112 can (i) receive the electrosurgical energy with a level of power and/or a waveform corresponding to the mode of operation selected via the user input device(s) 130 and (ii) supply the electrosurgical energy to the electrosurgical electrode 128.

In FIG. 1, the electrosurgical device 112 includes a plurality of electrical components that facilitate supplying the electrosurgical energy, which the electrosurgical device 112 receives from the electrosurgical generator 110, to the electrosurgical electrode 128. For example, the electrosurgical device 112 can include a printed circuit board 132 (e.g., a flexible printed circuit board), a housing conductor 134, one or more conductive leads 136, and/or a receptacle 137 that can provide a circuit for conducting the electrosurgical energy from the power cord 122 to the electrosurgical electrode 128. One or more of the electrical components can be positioned in the inner bore defined by the housing 124.

Within examples, the user input device(s) 130 can include one or more buttons on an exterior surface of the housing 124. Each button of the user input device(s) 130 can be operable to actuate a respective one of a plurality of switches 138 of the printed circuit board 132. In general, the switches 138 and/or the printed circuit board 132 are operable to control a supply of the electrosurgical energy from the electrosurgical generator 110 to the electrosurgical electrode 128. For instance, in one implementation, when each button is operated (e.g., depressed), the respective switch 138 associated with the button can be actuated to cause the printed circuit board 132 to transmit a signal to the electrosurgical generator 110 and cause the electrosurgical generator 110 to responsively supply the electrosurgical energy with a level of power and/or a waveform corresponding to a mode of operation associated with the button. In another implementation, operating the button and thereby actuating the respective switch 138 associated with the button can close the switch 138 to complete a circuit to the electrosurgical generator 110 to cause the electrosurgical generator 110 to responsively supply the electrosurgical energy with a level of power and/or a waveform corresponding to a mode of operation associated with the button. In some examples of this implementation, the printed circuit board 132 can be omitted.

In both example implementations, the electrosurgical energy supplied by the electrosurgical generator 110 can be supplied from (i) the power cord 122, the printed circuit board 132, and/or the switches 138 to (ii) the electrosurgical electrode 128 by the housing conductor 134 and the conductive lead(s) 136. As such, as shown in FIG. 1, the printed circuit board 132 can be coupled to the power cord 122, the housing conductor 134 can be coupled to the printed circuit board 132 and the conductive lead(s) 136, and the conductive lead(s) 136 can be coupled to the electrosurgical electrode 128 (e.g., via the receptacle 137). In this arrangement, the housing conductor 134 can conduct the electrosurgical energy (supplied to the housing conductor 134 via the printed circuit board 132) to the conductive lead(s) 136, and the conductive lead(s) 136 and the receptacle 137 can conduct the electrosurgical energy to the electrosurgical electrode 128.

In general, the housing conductor 134 can include one or more conductive elements that provide an electrically conductive bus for supplying the electrosurgical energy to the electrosurgical electrode 128. In one example, the housing conductor 134 can be formed in a helical shape. In this arrangement, the housing conductor 134 can be compressible and expandable such that the housing conductor 134 can accommodate the shaft 126 telescopically moving into and/or out of the housing 124 to retract and/or extend, respectively, the electrosurgical electrode 128 relative to the housing 124. In another example, the conductive lead(s) 136 can include one or more wires. In another example, the conductive lead(s) 136 can include one or more conductive traces formed by, for instance, screen printing, sputtering, electroplating, conductive paint, and/or laser ablation.

Within examples, the conductive lead(s) 136 can extend from the housing conductor 134 to the electrosurgical electrode 128. In one example, the conductive lead(s) 136 can include one or more wires. In another example, the conductive lead(s) 136 can include one or more conductive traces formed by, for instance, screen printing, sputtering, electroplating, conductive paint, and/or laser ablation. The conductive lead(s) 136 can be disposed in an internal conduit of the shaft 126 and an exterior surface of the shaft 126 can be formed of an electrically insulating material. This can help reduce (or prevent) loss of the electrosurgical energy prior to the electrosurgical electrode 128.

The receptacle 137 can couple the electrosurgical electrode 128 to the electrosurgical device 112. As an example, the receptacle 137 and the electrosurgical electrode 128 can be configured to couple to each other by friction-fit. Accordingly, the receptacle 137 and the electrosurgical electrode 128 can have respective sizes and/or respective shapes that provide for a friction-fit coupling between the receptacle 137 and the electrosurgical electrode 128 when the electrosurgical electrode 128 is inserted in the receptacle 137. This can allow for the electrosurgical electrode 128 to be releasably coupled to the electrosurgical device 112, which can facilitate an interchangeability of a plurality of the electrosurgical electrodes 128 with the electrosurgical device 112. The receptacle 137 and electrosurgical electrode 128 can be mechanically keyed to ensure the correct electrical connections are made. In other examples, the electrosurgical electrode 128 can be coupled to the receptacle 137 by another type of releasable coupling (e.g., a threaded coupling) or a non-releasable coupling (e.g., via welding and/or soldering).

Within examples, the receptacle 137 can also include a conductor that can electrically couple the electrosurgical electrode 128 to the electrosurgical energy supplied to the electrosurgical device 112 by the electrosurgical generator 110. For instance, the receptacle 137 can be electrically coupled to the conductive lead(s) 136 (e.g., by a conductive material).

As shown in FIG. 1, the electrosurgical device 112 can additionally include a light source 140 that is configured to emit light. In the example of FIG. 1, the light source 140 can be optically coupled to an optical waveguide 142, which is configured to receive the light emitted by the light source 140 and transmit the light in a distal direction toward a surgical site to illuminate the surgical site while performing electrosurgery using the electrosurgical electrode 128. Within examples, the optical waveguide 142 can transmit the light in the distal direction via total internal reflection. For instance, the optical waveguide can include a cladding and/or an air gap on an exterior surface of the optical waveguide 142. In some implementations, the optical waveguide 142 can be formed as a single, monolithic structure.

In another example, the electrosurgical device 112 can omit the optical waveguide 142 and instead emit the light from the light source 140 directly to the surgical field without transmitting the light through the optical waveguide 142. In another example, the electrosurgical device 112 can include one or more optical fibers in addition or alternative to the optical waveguide 142, and the optical fiber(s) can transmit the light emitted by the light source 140 in the distal direction toward the surgical site.

In FIG. 1, the light source 140 is coupled to the shaft 126. As such, the light source 140 can also move telescopically with the shaft 126 relative to the housing 124. However, in other examples, the light source 140 can be in the interior bore of the housing 124 and/or coupled to an exterior surface of the housing 124. As examples, the light source 140 can include one or more light emitting diodes (LEDs), organic light emitting diodes (OLEDs), optical fibers, non-fiber optic waveguides, and/or lenses.

The optical waveguide 142 can be at a distal end of the shaft 126. In some examples, the electrosurgical electrode 128 can extend from a central portion of the optical waveguide 142. As such, the optical waveguide 142 can circumferentially surround the electrosurgical electrode 128 to emit the light distally around all sides of the electrosurgical electrode 128. This can help to mitigate shadows and provide greater uniformity of illumination in all rotational alignments of the shaft 126 relative to the housing 124 and/or the electrosurgical device 112 relative to the target tissue.

In implementations that include the light source 140, the user input device(s) 130, the printed circuit board 132, the switches 138, the housing conductor 134, and/or the conductive lead(s) 136 can additionally supply an electrical power from a direct current (DC) power source 144 to the light source 140. In one example, the DC power source 144 can include a battery disposed in the housing 124 and/or the plug of the power cord 122. Although the electrosurgical device 112 includes the DC power source 144 in FIG. 1, the DC power source 144 can be separate and distinct from the electrosurgical device 112 in other examples. For instance, in another example, the electrosurgical generator 110 can include the DC power source 144.

Additionally, in implementations that include the light source 140, the user input device(s) 130 can be operable to cause the light source 140 to emit the light. In one example, the user input device(s) 130 can include a button that independently controls the light source 140 separate from the button(s) that control the electrosurgical operational modes of the electrosurgical device 112. In another example, the user input device(s) 130 and the printed circuit board 132 can be configured such that operation of the button(s) that control the electrosurgical operational mode simultaneously control operation of the light source 140 (e.g., the light source 140 can be automatically actuated to emit light when a button is operated to apply the electrosurgical energy at the electrosurgical electrode 128).

As shown in FIG. 1, responsive to operation of the user input device(s) 130 to actuate the light source 140, the DC power source 144 can supply the electrical power (e.g., a DC voltage) to the light source 140 via the printed circuit board 132, the housing conductor 134, and/or the conductive lead(s) 136. In this implementation, one or more of the conductive elements of the housing conductor 134 can be configured to supply the electrical power from the DC power source 144 to the light source 140 and/or return the electrical power from the light source 140 to the DC power source 144. Accordingly, the housing conductor 134 can additionally or alternatively assist in providing electrical communication between the DC power source 144 and the light source 140 as the shaft 126 and the light source 140 telescopically move relative to the housing 124.

As noted above, the electrosurgical device 112 can additionally include features that provide for evacuating surgical smoke from a target tissue to a location external to the surgical site. Surgical smoke is a by-product of various surgical procedures. For example, during surgical procedures, surgical smoke may be generated as a by-product of electrosurgical units (ESU), lasers, electrocautery devices, ultrasonic devices, and/or other powered surgical instruments (e.g., bones saws and/or drills). In some instances, the surgical smoke may contain toxic gases and/or biological products that result from a destruction of tissue. Additionally, the surgical smoke may contain an unpleasant odor. For these and other reasons, many guidelines indicate that exposure of surgical personnel to surgical smoke should be reduced or minimized.

To reduce (or minimize) exposure to surgical smoke, a smoke evacuation system may be used during the surgical procedure. In general, the smoke evacuation system may include a suction pump 146 that can generate sufficient suction and/or vacuum pressure to draw the surgical smoke away from the surgical site. In some implementations, the smoke evacuation system may be coupled to an exhaust system (e.g., an in-wall exhaust system) that exhausts the surgical smoke out of an operating room. In other implementations, the smoke evacuation system may filter air containing the surgical smoke and return the air to the operating room. Within examples, the suction pump 146 and the electrosurgical generator 110 can be provided as separate devices or integrated in a single device (e.g., in a common housing).

As shown in FIG. 1, the shaft 126 can include a smoke evacuation channel 148 at a distal end of the shaft 126. In an example, the smoke evacuation channel 148 can extend circumferentially around the optical waveguide 142 at the distal end of the shaft 126. The smoke evacuation channel 148 can also include a smoke inlet that circumferentially surrounds the optical waveguide 142 at the distal end of the shaft 126. In this arrangement, the smoke inlet of the smoke evacuation channel can help to receive surgical smoke into the smoke evacuation channel 148 in all rotational alignments of the shaft 126 relative to the housing 124 and/or the electrosurgical device 112 relative to the target tissue. However, in another example, the smoke evacuation channel 148 can include one or more smoke inlets that do not extend circumferentially around the optical waveguide 142 and/or the electrosurgical electrode 128.

In some implementations, the smoke evacuation channel 148 and the optical waveguide 142 can be coaxial. For instance, the smoke evacuation channel 148 and the optical waveguide 142 can each have a longitudinal axis that is aligned with a central axis of the shaft 126. In other implementations, the smoke evacuation channel 148 and the optical waveguide 142 can have respective longitudinal axes that are offset relative to each such that the smoke evacuation channel 148 and the optical waveguide 142 are not coaxial.

In an example, the smoke evacuation channel 148 can include an outer tube that is separated from the optical waveguide 142 by an air gap. For instance, the shaft 126 can include a plurality of standoffs that extend between the optical waveguide 142 and the outer tube of the smoke evacuation channel 148 to provide the air gap between the outer tube and the optical waveguide 142. In one implementation, the optical waveguide 142 can include the standoffs such that the optical waveguide 142 and the standoffs are formed as a single, monolithic structure. In another implementation, the standoffs can be formed as a single, monolithic structure with the outer tube of the smoke evacuation channel 148. In another implementation, the standoffs can be separate from the outer tube of the smoke evacuation channel 148 and the optical waveguide 142.

In an example, the smoke evacuation channel 148 of the shaft 126 defines a first portion of a smoke flow path, and the interior bore 125 of the housing 124 defines a second portion of a smoke flow path. FIG. 2 illustrates a partial cross-sectional view of the electrosurgical device 112 according to an implementation of this example. In this arrangement, the surgical smoke can be received from the surgical site into the smoke evacuation channel 148 of the shaft 126, and flow proximally along the smoke evacuation channel 148 to the interior bore 125 of the housing 124. In the interior bore 125 of the housing 124, the smoke can further flow to a smoke tube 150 that is coupled to a proximal end of the housing 124 and configured to convey smoke from the housing 124 to the suction pump 146.

In another example, the housing 124 includes an interior wall separating the interior bore 125 from a smoke evacuation chamber 152 in the housing 124. The smoke evacuation channel 148 of the shaft 126 is in fluid communication with the smoke evacuation chamber 152 of the housing 124. In this example, the smoke evacuation channel 148 of the shaft 126 defines a first portion of a smoke flow path, and the smoke evacuation chamber 152 of the housing 124 defines a second portion of a smoke flow path. FIG. 3 illustrates a partial cross-sectional view of the electrosurgical device 112 according to an implementation of this example. Accordingly, in this example, the smoke is routed through the smoke evacuation chamber 152, which is separate from the interior bore 125, to the smoke tube 150 at the proximal end of the housing 124. This can beneficially help to mitigate exposing one or more components of the electrosurgical device 112 to the surgical smoke in the housing 124. In some implementations, providing a separate smoke evacuation chamber 152 can additionally or alternatively help to improve the flow of surgical smoke by reducing (or eliminating) obstacles and impediments to gas flows along the second portion of the flow path.

In one implementation, a proximal portion of the smoke evacuation channel 148 comprises at least one aperture 354, and the interior wall of the housing 124 includes at least one slot. The at least one aperture 354 of the smoke evacuation channel 148 can be aligned with the at least one slot 358 of the interior wall 356 of the housing 124 such that the smoke evacuation channel 148 of the shaft 126 is in fluid communication with the smoke evacuation chamber 152 of the housing 124. The at least one aperture 354 is axially movable along the at least one slot 358 when the shaft 126 telescopically moves relative to the housing 124 such that the smoke evacuation channel 148 of the shaft 126 is in fluid communication with the smoke evacuation chamber 152 of the housing 124 when the shaft 126 telescopically moves relative to the housing 124.

In an example, the at least one aperture 354 includes a plurality of apertures 354 and the at least one slot 358 includes a plurality of slots 358. Also, in this example, each apertures 354 is aligned with a respective one of the plurality of slots 358, and the shaft 126 is rotatable relative to the housing 124, and the plurality of apertures 354 and the plurality of slots 358 are arranged around a circumference of the shaft 126 such that fluid communication between the smoke evacuation channel 148 and the smoke evacuation chamber 152 is maintained when the shaft 126 is rotated relative to the housing 124. In one implementation, the interior wall 356 and the slot(s) 358 can rotate together with the shaft 126 and the aperture(s) 354. By providing a plurality of apertures 354 and respective slots 358, at least one pair of aperture 354 and slot 358 can be rotationally aligned with the smoke evacuation chamber 152 and thereby provide fluid communication between the smoke evacuation channel 148 and the smoke evacuation chamber 152.

Figure 4:
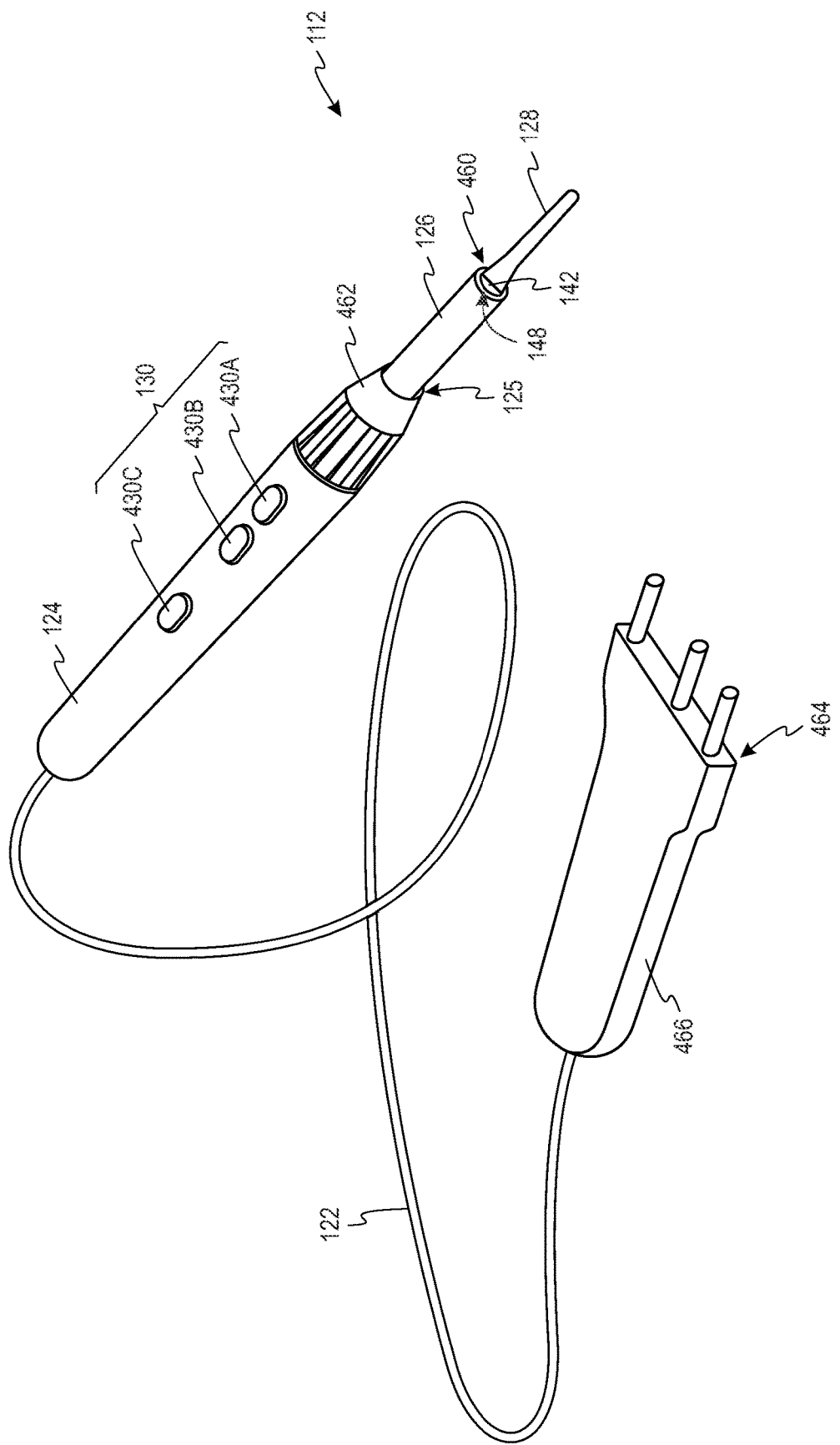
FIG. 4 depicts a perspective view of an electrosurgical device, according to an example.

Referring now to FIG. 4, a perspective view of an implementation of the electrosurgical device 112 is shown according to an example. As shown in FIG. 4, the electrosurgical device 112 includes the housing 124 defining the interior bore 125, the shaft 126 telescopically moveable in the interior bore 125 of the housing 124, and the electrosurgical electrode 128 coupled to the shaft 126. However, as described above, the shaft 126 can be fixedly coupled to the housing 124 such that the shaft 126 is not moveable relative to the housing 124 in other examples.

Additionally, in FIG. 4, the optical waveguide 142 is at a distal end 460 of the shaft 126. In this arrangement, the optical waveguide 142 can telescopically move with the shaft 126 relative to the housing 124. In FIG. 4, the optical waveguide 142 extends around the electrosurgical electrode 128. This can help to emit the light in a relatively uniform manner by reducing (or preventing) shadows due to an orientation of the optical waveguide 142 and the electrosurgical electrode 128 relative to the surgical site. However, in other examples, the optical waveguide 142 may not extend entirely around the electrosurgical electrode 128 at the distal end 460 of the shaft 126, and/or the optical waveguide 142 can be at a different position on the shaft 126 and/or the housing 124.

In some examples, the electrosurgical device 112 can include a collar 462 at a proximal end of the housing 124. The collar 462 can be rotatable relative to the housing 124 to increase and/or decrease friction between an outer surface of the shaft 126 and an inner surface of the collar 462. In this way, the collar 462 to allow and/or inhibit axial telescopic movement of the shaft 126 relative to the housing 124.

As shown in FIG. 4, the electrosurgical device 112 includes the power cord 122. At a proximal end 464 of the power cord 122, the power cord 122 includes a plug 466 configured to couple to the connector 120 of the electrosurgical generator 110. A distal end of the power cord 122 is coupled to the printed circuit board 132 in an interior cavity of the housing 124. In this arrangement, the power cord 122 extends proximally from the housing 124 to the plug 466.

Additionally, as shown in FIG. 4, the user input device(s) 130 include a first button 430A, a second button 430B, and a third button 430C on an exterior surface of the housing 124. In one implementation, the first button 430A can be actuated to operate the electrosurgical device 112 in a cutting mode of operation, the second button 430B can be actuated to operate the electrosurgical device 112 in a coagulation mode of operation, and the third button 430C can be actuated to operate the light source 140 (i.e., to cause the light source 140 to emit light or cease emitting light). As described above, the user input device(s) 130 can be configured differently in other examples. For instance, the electrosurgical device 112 can be operable in a lesser quantity of modes of operation, a greater quantity of modes of operation, and/or different types of modes of operation in other examples (e.g., such as the example modes of operation described above). Additionally, for instance, the at least one user input device 130 can additionally or alternatively include the user interface 116 of the electrosurgical generator 110 and/or another external device (e.g., a footswitch) for operating the electrosurgical device 112 in one or more modes of operation.

Figure 5:
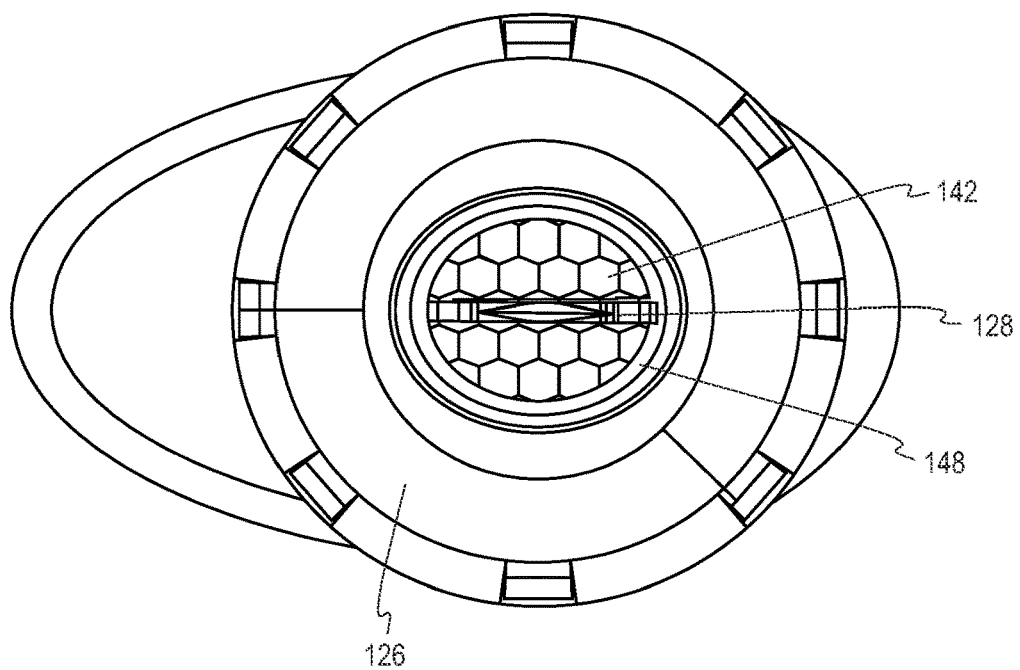
FIG. 5 depicts a distal end of an electrosurgical device, according to an example.
Figure 6:
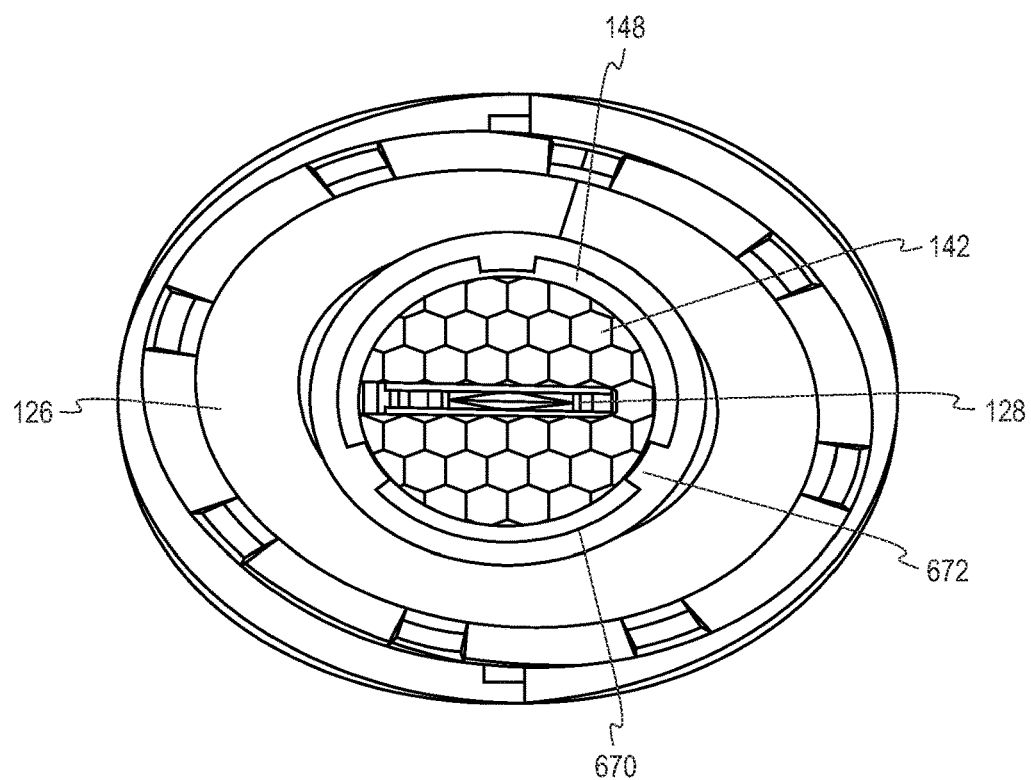
FIG. 6 depicts a distal end of an electrosurgical device, according to another example.

FIGS. 5-6 illustrate a distal end of the electrosurgical device 112 according to examples. As shown in FIGS. 5-6, the shaft 126 includes the optical waveguide 142 at a distal end of the shaft 126, and the smoke evacuation channel 148 circumferentially surrounding the optical waveguide 142 at the distal end of the shaft 126. As shown in FIG. 6, the smoke evacuation channel 148 can include an outer tube 670 that is separated from the optical waveguide 142 by a plurality of standoffs 672.

Figure 7A:
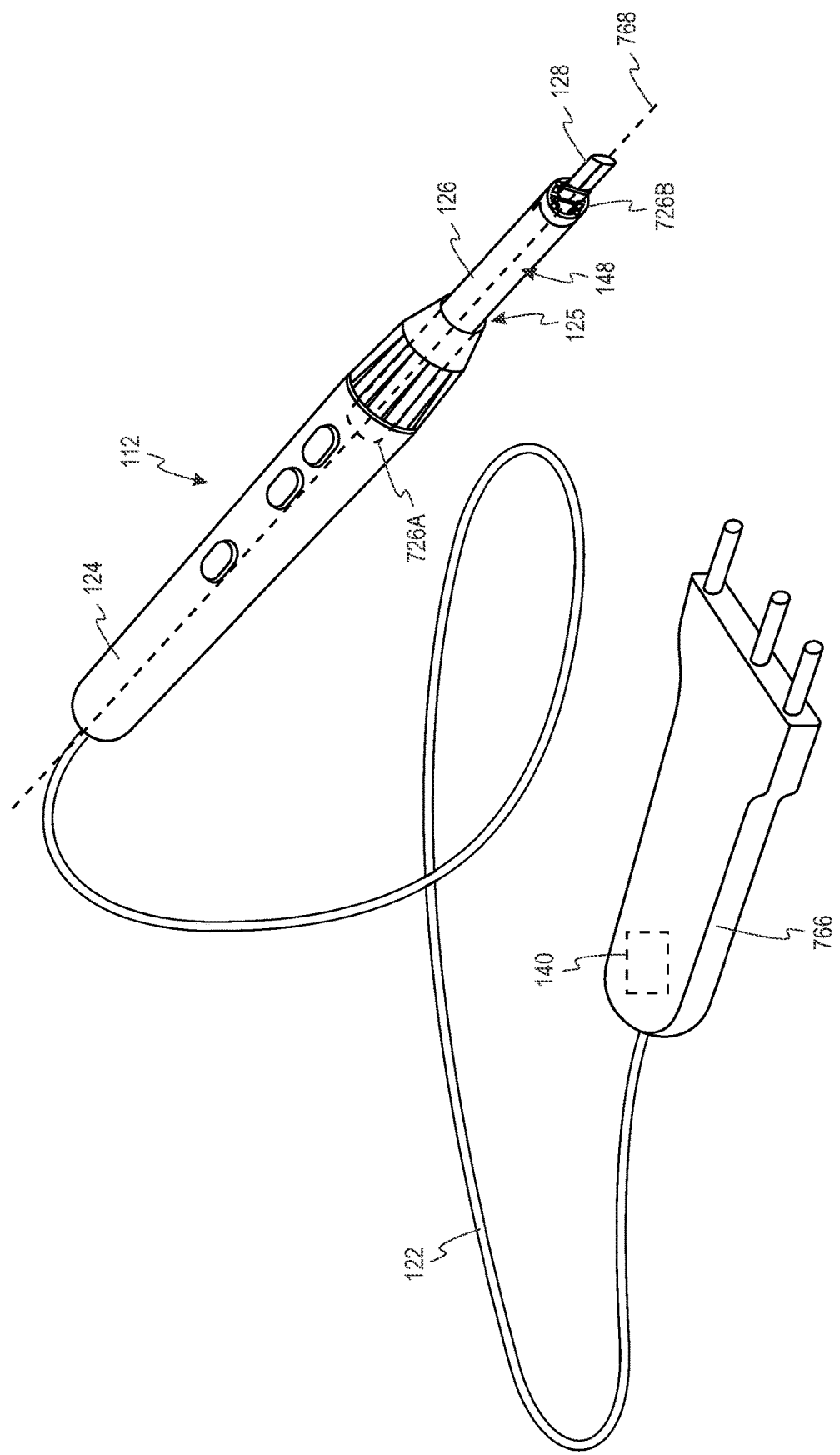
FIG. 7A depicts a perspective view of an electrosurgical device, according to another example.
Figure 7B:
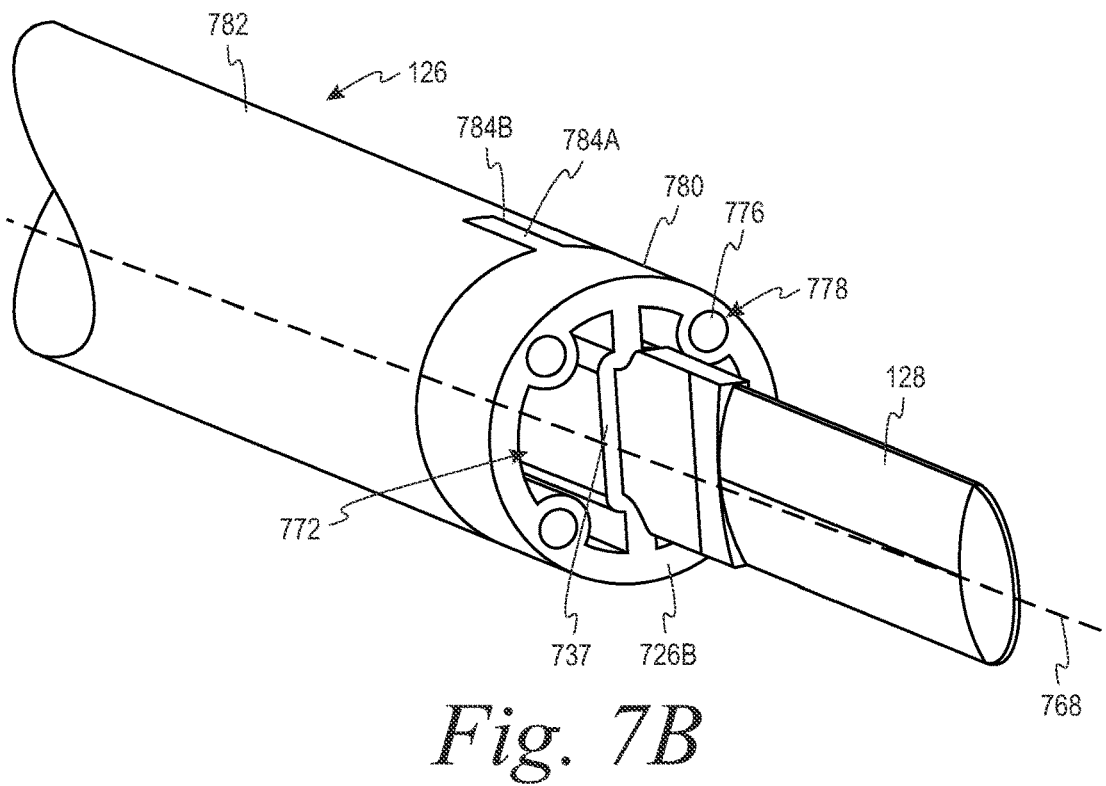
FIG. 7B depicts a perspective view of a distal portion of the electrosurgical device shown in FIG. 7A, according to an example.
Figure 7C:
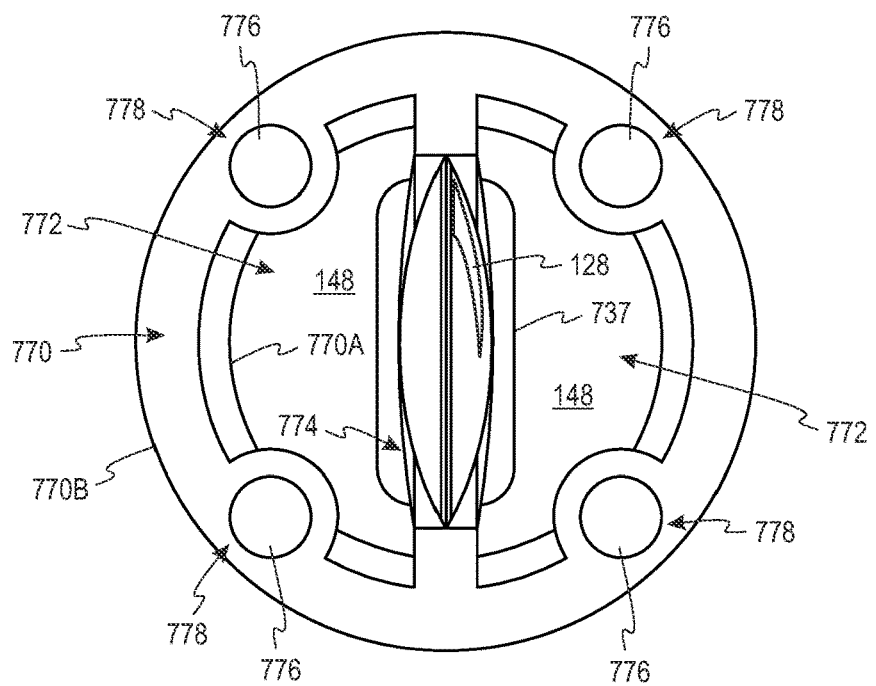
FIG. 7C depicts shows a side view of the electrosurgical device shown in FIG. 7A, according to an example

Referring now to FIGS. 7A-7C, an implementation of the electrosurgical device 112 is shown according to another example. In particular, FIG. 7A shows a perspective view of the electrosurgical device 112, FIG. 7B shows a perspective view of a distal portion of the electrosurgical device 112, and FIG. 7C shows a side view of the electrosurgical device 112 according to this example.

As shown in FIG. 7A, the electrosurgical device 112 includes the housing 124 defining the interior bore 125, the shaft 126 telescopically moveable in the interior bore 125 of the housing 124, and the electrosurgical electrode 128 coupled to the shaft 126. The shaft 126 has a longitudinal axis 768 extending from a proximal end 726A of the shaft 126 to a distal end 726B of the shaft 126. Although the shaft 126 is telescopically moveable relative to the housing 124 in FIGS. 7A-7C, the shaft 126 can be fixedly coupled to the housing 124 such that the shaft 126 is not moveable relative to the housing 124 in other examples.

As shown in FIGS. 7B-7C, the shaft 126 includes a shaft wall 770 having an inner surface 770A and an outer surface 770B. The inner surface 770A of the shaft wall 770 defines the smoke evacuation channel 148 that extends from the distal end 726B of the shaft 126 to the proximal end 726A of the shaft 126. As described above, the smoke evacuation channel 148 can provide the first portion of the smoke flow path along which surgical smoke flows as the surgical smoke is evacuated from a surgical site by the electrosurgical device 112.

For instance, in one example, the smoke evacuation channel 148 of the shaft 126 can define the first portion of the smoke flow path, and the interior bore 125 of the housing 124 can define the second portion of a smoke flow path as described above with respect to FIG. 2. In this example, the smoke received from the surgical site into the smoke evacuation channel 148 of the shaft 126 can flow proximally along the smoke evacuation channel 148 to the interior bore 125 of the housing 124. In the interior bore 125 of the housing 124, the smoke can further flow to the smoke tube 150 (shown in FIG. 1) that is coupled to a proximal end of the housing 124 and configured to convey the smoke from the housing 124 to the suction pump 146 (shown in FIG. 1).

In another example, the smoke evacuation channel 148 of the shaft 126 can define the first portion of the smoke flow path, and the smoke evacuation chamber 152 of the housing 124 can define the second portion of the smoke flow path as described above with respect to FIG. 3. In this example, as described above, the smoke can be routed through the smoke evacuation chamber 152 (shown in FIGS. 1 and 3), which is separate from the interior bore 125, to the smoke tube 150 at the proximal end of the housing 124. This can beneficially help to mitigate exposing one or more components of the electrosurgical device 112 to the surgical smoke in the housing 124. In some implementations, providing a separate smoke evacuation chamber 152 can additionally or alternatively help to improve the flow of surgical smoke by reducing (or eliminating) obstacles and impediments to gas flows along the second portion of the flow path.

As noted above, the electrosurgical electrode 128 is coupled to the shaft 126. More specifically, in FIGS. 7A-7C, the electrosurgical device 112 includes an electrode receptacle 737 that couples the electrosurgical electrode 128 to the shaft 126. As shown in FIGS. 7B-7C, the electrode receptacle 737 extends across the smoke evacuation channel 148 in a direction that is transverse to the longitudinal axis 768 of the shaft 126 such that electrode receptacle 737 partitions the smoke evacuation channel 148 into a plurality of smoke inlets 772 at the distal end 726B of the shaft 126. As such, the smoke inlets 772 can be located on a plurality of sides of the electrode receptacle 337 and the electrosurgical electrode 128 (e.g., a first smoke inlet 772 can be adjacent a first major surface of the electrosurgical electrode 128 and a second smoke inlet 772 can be adjacent a second, opposing major surface of the electrosurgical electrode 128). In this arrangement, the smoke inlets 772 of the smoke evacuation channel 148 can help to receive surgical smoke into the smoke evacuation channel 148 in all rotational alignments of the shaft 126 relative to the housing 124 and/or the electrosurgical device 112 relative to the target tissue.

In one example, a cross-sectional area of the smoke inlets 772 can be at least 50% of a cross-sectional area of the smoke evacuation channel 148. In another example, the cross-sectional area of the smoke inlets 772 can be at least 75% of the cross-sectional area of the smoke evacuation channel 148. In another example, the cross-sectional area of the smoke inlets 772 can be at least 80% of the cross-sectional area of the smoke evacuation channel 148. In another example, the cross-sectional area of the smoke inlets 772 can be at least 85% of the cross-sectional area of the smoke evacuation channel 148. Accordingly, the electrode receptacle 737 can help to achieve a relatively large cross-sectional area of the smoke inlets 772 (and the smoke evacuation channel 148), which can help to increase smoke evacuation performance of the electrosurgical device 112.

In FIG. 7C, a first one of the smoke inlets 772 is defined by a first side of the electrode receptacle 737 and a first portion of the inner surface 770A of the shaft wall 770, and a second one of the smoke inlets 772 is defined by a second side of the electrode receptacle 737 and a second portion of the inner surface 770A of the shaft wall 770. In some examples, the smoke inlets 772 can have a common size and/or a common shape. This can help to provide relatively balanced suction on the first side of the electrode receptacle 737 and the second side of the electrode receptacle 737. However, in other examples, at least one of the smoke inlets 772 can have a different size and/or a different shape than another one of the smoke inlets 772.

Within examples, the electrode receptacle 737 can define an aperture 774 that can receive the electrosurgical electrode 128, and the electrosurgical electrode 128 can be coupled to the electrode receptacle 737 by a releasable coupling (e.g., friction-fit or a threaded coupling) or a non-releasable coupling (e.g., via welding and/or soldering). The aperture 774 can be aligned with a center axis of the shaft 126 such that the electrosurgical electrode 128 is centered on the distal end 726B of the shaft 126. This can help to provide for relatively good visibility of the electrosurgical electrode 128 and the surgical site. Additionally, the center location of the electrosurgical electrode 128 can help to provide for operating the electrosurgical device 112 in a plurality of rotational alignments between the electrosurgical electrode 128 relative to the housing 124 and/or between the electrosurgical device 112 relative to the surgical site.

As noted above, in some examples, the electrosurgical device 112 can include one or more optical fibers in addition or alternative to the optical waveguide 142 for transmitting the light distally from the light source 140 to the surgical field. FIGS. 7A-7C depict an example in which the electrosurgical device 112 includes a plurality of optical fibers 776 extending from the proximal end 726A of the shaft 126 to the distal end 726B of the shaft 126. In the example of FIGS. 7A-7C, the electrosurgical device 112 omits the optical waveguide 142. However, the electrosurgical device 112 shown in FIGS. 7A-7C can include the optical waveguide 142 in addition or alternative to the optical fibers 776 in another example.

As shown in FIG. 7A, the electrosurgical device 112 includes the light source 140 coupled to the plurality of optical fibers 776 at a position that is proximal of the proximal end 726A of the shaft 126. In one example, the light source 140 can be in the housing 124 proximal of the shaft 126. In another example, as shown in FIG. 7A, the electrosurgical device 112 includes the power cord 122 extending proximally from the housing 124 to a plug 766, and the light source 140 is located in a housing of the plug 766. This can help to reduce (or eliminate) elevated temperatures in the housing 124 and/or the shaft 126 of the electrosurgical device 112. In an implementation, each optical fiber 776 can extend from the light source 140 in the plug 766 to the distal end 726B of the shaft 126. In this implementation, the optical fibers 776 can extend through the power cord 122, the interior bore 125 of the housing 124, and the smoke evacuation channel 148 of the shaft 126.

At the distal end 726B of the shaft 126, the optical fibers 776 can be coupled to a plurality of conduits 778, which can provide for fixedly positioning light-emitting ends of the optical fibers 776 relative to the distal end 726B of the shaft 126 and/or the electrosurgical electrode 128. The optical fibers 776 can be coupled to the respective conduits 778 by, for instance, a friction-fit coupling, an adhesive coupling, and/or a welded coupling.

As shown in FIG. 7C, the conduits 778 can extend through the shaft wall 770 between the inner surface 770A and the outer surface 770B, and each optical fiber 776 can be in a respective one of the conduits 778. This can provide for positioning the light-emitting ends of the optical fibers 776 at a periphery of the shaft 126, which can help to reduce (or minimize) the formation of shadows on the surgical site. In some examples, the light-emitting ends of the optical fibers 776 can be arranged in a plane that is approximately perpendicular to the longitudinal axis 768 (e.g., parallel with a plane of the distal end 726B of the shaft 126). In other examples, one or more of the light-emitting ends of the optical fibers 776 can be arranged at a different angle relative to the longitudinal axis 768 (e.g., angled inwardly toward the longitudinal axis 768 and/or angled outwardly away from the longitudinal axis 768).

In FIGS. 7A-7C, a quantity of the conduits 778 is four, and a quantity of the optical fibers 776 is four. However, the electrosurgical device 112 can include a lesser quantity or a greater quantity of the conduits 778 and the optical fibers 776 in other examples. In some examples, the quantity of the conduits 778 and the optical fibers 776 can be at least two. This can help to illuminate the surgical field around the electrosurgical electrode 128 and thereby mitigate (or eliminate) the formation of shadows on the surgical field. In FIGS. 7A-7C, the conduits 778 and the optical fibers 776 are equally spaced from each other around the periphery of the shaft 126. This can also help to illuminate the surgical field around the electrosurgical electrode 128 and thereby mitigate (or eliminate) the formation of shadows on the surgical field.

In some implementations, the light-emitting ends of the optical fibers 776 can include one or more optical structures that can help to shape the light emitted from the optical fibers 776. As examples, the one or more optical structures can be selected from a group consisting of: one or more lenses, one or more prisms, one or more facets, and one or more optical filters.

In one implementation, the electrode receptacle 737 and a remainder of the shaft 126 can be integrally formed as a single-piece, monolithic structure. In another implementation, the shaft 126 can be formed as multi-part construction. For instance, in FIGS. 7A-7C, the shaft 126 can include a distal end portion 780 coupled to a main body portion 782, and the distal end portion 780 can include the electrode receptacle 737. In this example, the distal end portion 780 is press-fit into the main body portion 782 of the shaft 126. In other examples, the distal end portion 780 can be additionally or alternatively coupled to the main body portion 782 by an adhesive, bonding, welding, and/or soldering.

Within examples, the distal end portion 780 and the main body portion 782 can include one or more alignment features that facilitate coupling the distal end portion 780 and the main body portion 782 in a predetermined rotational alignment relative to each other. For instance, in FIG. 7B, the distal end portion 780 includes a protrusion 784A and the main body portion 782 includes a slot 784B that receives the protrusion 784A when the distal end portion 780 is coupled to the main body portion 782 of the shaft 126. The alignment features of the distal end portion 780 of the shaft 126 and the main body portion 782 of the shaft 126 can help to arrange the electrosurgical electrode 128 is a predetermined orientation relative to other features of the electrosurgical device 112 such as, for instance, the user input device(s) 130.

In FIGS. 7A-7C, the distal end portion 780 of the shaft 126 includes the conduits 778 extending through the shaft wall 770 between the inner surface 770A and the outer surface 770B. In an implementation, the main body portion 782 can omit the conduits 778. In this implementation, each optical fiber 776 can be fixedly coupled to the shaft wall 770 by a respective one of the conduits 778 at the distal end portion 780 and can be unsecured to the shaft wall 770 in the main body portion 782 of the shaft 126. In another implementation, the main body portion 782 can additionally include the conduits 778 to couple the optical fibers 776 to the shaft wall 770 in the main body portion 782.

In the example described above and shown in FIGS. 7A-7C, the optical fibers 776 are coupled to the shaft 126 by the conduits 778. In other examples, the optical fibers 776 can be additionally or alternatively coupled to shaft 126 by other optical fiber retainer structures such as, for instance, one or more clips and/or one or more grooves in which the optical fibers can be retained by a friction-fit coupling.

In the example shown in FIGS. 7A-7C, the electrosurgical device 112 includes four conduits 778 and four optical fibers 776 equally spaced from each other around the periphery of the shaft 126. As described above, the electrosurgical device 112 can include a lesser quantity or a greater quantity of the conduits 778 and the optical fibers 776 in other examples. For instance, FIGS. 8A-8B depict a distal end portion 880 of the shaft 126 that includes two conduits 878A, 878B that can couple two optical fibers 776 to the shaft 126, according to another example.

As shown in FIGS. 8A-8B, the conduits 878A, 878B can include a first conduit 878A and a second conduit 878B. In this example, an electrode receptacle 837 extends across the smoke evacuation channel 148 between the first conduit 878A and the second conduit 878B. In this arrangement, the distal end portion 880 is configured to couple a first optical fiber and a second optical fiber on opposing sides of the electrosurgical electrode 128 when the electrosurgical electrode 128 is disposed in an aperture 874 of the electrode receptacle 837. This can help to emit light on a plurality of sides of the electrosurgical electrode 128 and thereby reduce (or prevent) forming shadows on the surgical site.

Additionally, as shown in FIG. 8A, the distal end portion 880 of the shaft 126 can include a proximal-extension 886 that extends proximally from the distal end 726B of the shaft 126. Within examples, the distal end portion 780 shown in FIGS. 7A-7C can also include or omit the proximal-extension 886. The proximal-extension 886 can be sized and/or shaped such that the proximal-extension 886 can be received into the smoke evacuation channel 148 of the main body portion 782 when the distal end portion 880 is coupled to the main body portion 782. For instance, the proximal-extension 886 can have dimensions that are relatively smaller than dimensions of the shaft wall 770 at the main body portion 782 to allow the main body portion 882 to receive the proximal-extension 886 of the distal end portion 880. The proximal-extension 886 received in the main body portion 782 can help to provide for a friction-fit coupling between the distal end portion 880 and the main body portion 782, and/or improve a strength of the coupling between the distal end portion 880 and the main body portion 782.

Figure 9A:
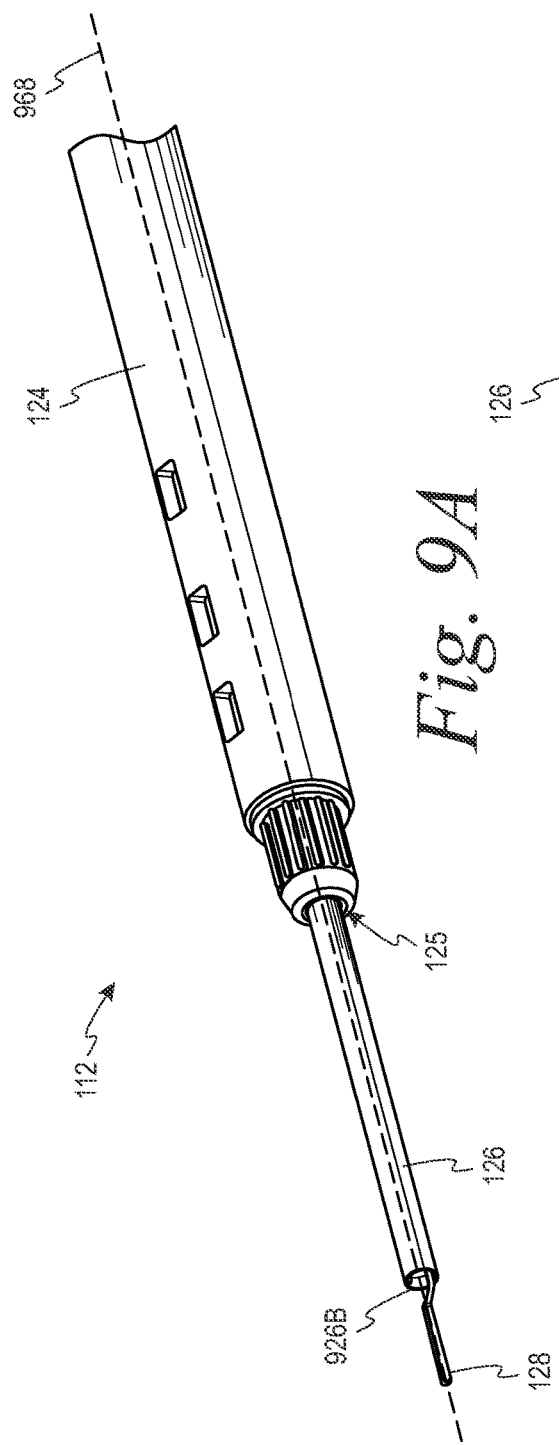
FIG. 9A depicts a perspective view of an electrosurgical device, according to another example.
Figure 9C:
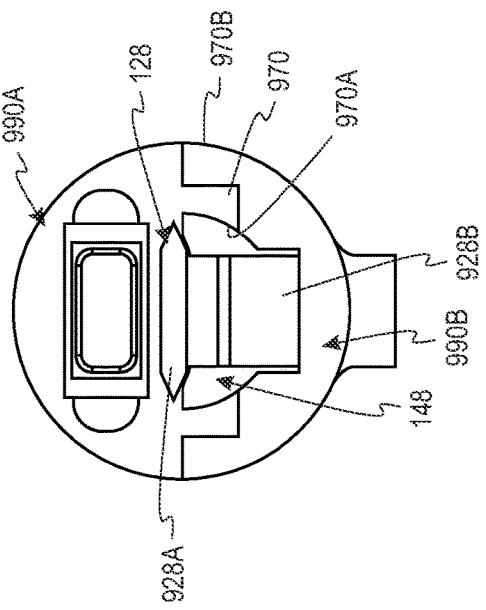
FIG. 9C depicts a side view of the distal end of the shaft shown in FIG. 9B, according to an example.
Figure 9B:
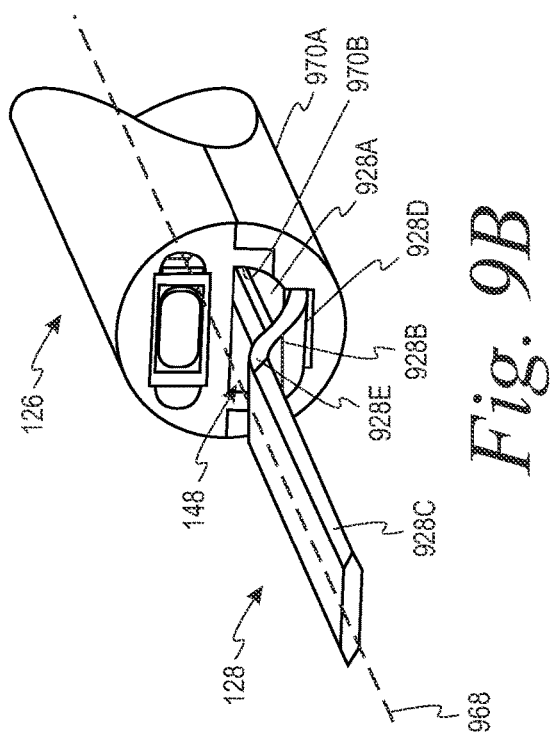
FIG. 9B depicts a perspective view of a distal end of a shaft of the electrosurgical device shown in FIG. 9A, according to an example.
Figure 9D:
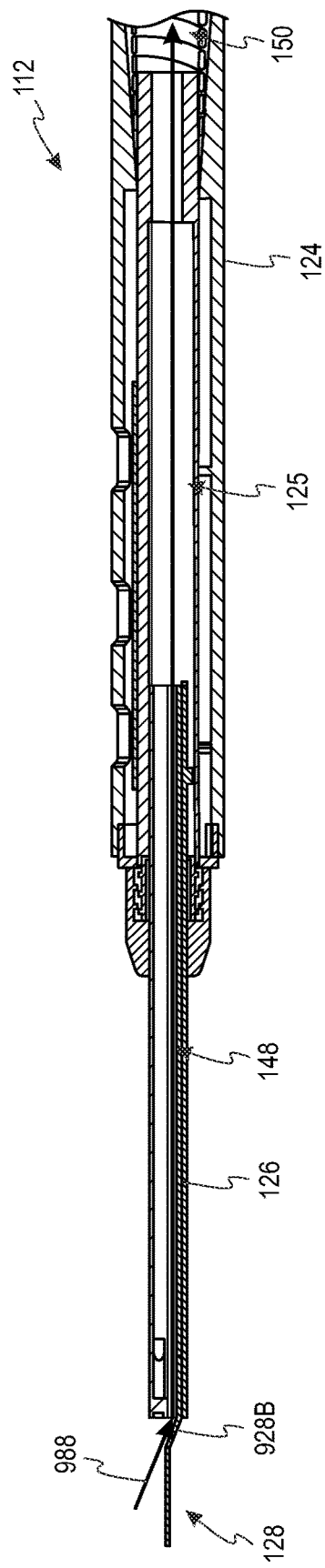
FIG. 9D depicts a cross-sectional view of the electrosurgical device shown in FIG. 9A, according to an example.
Figure 9E:
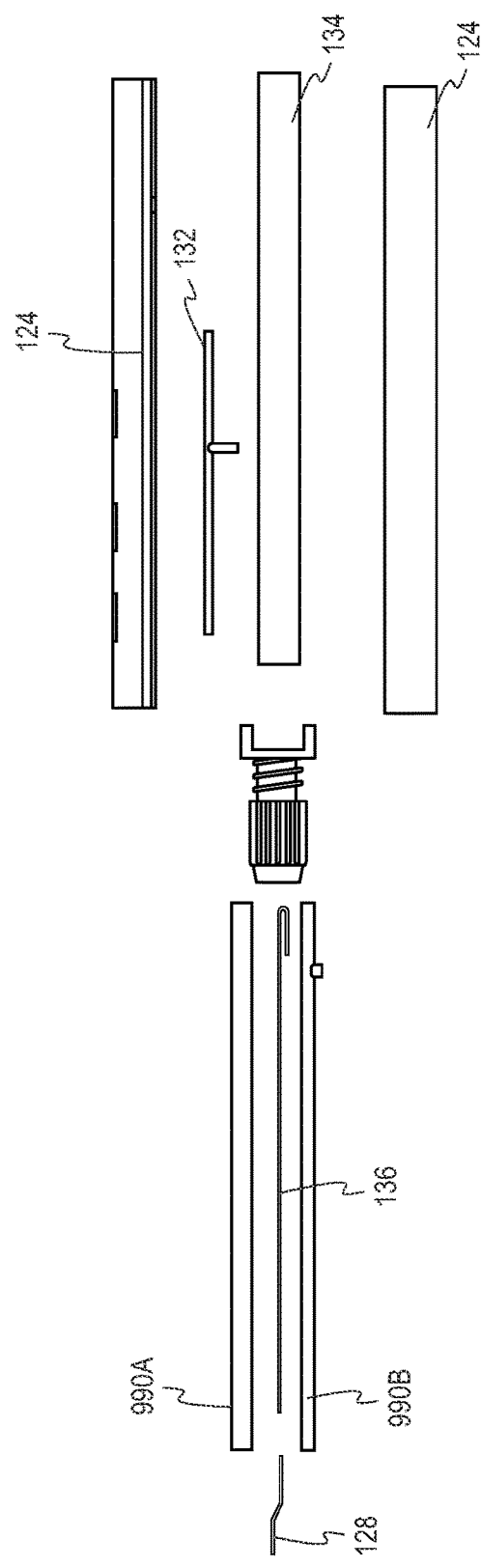
FIG. 9E depicts an exploded view of the electrosurgical device shown in FIG. 9A, according to an example.

Referring now to FIGS. 9A-9E, an implementation of the electrosurgical device 112 is shown according to another example. In particular, FIG. 9A shows a perspective view of the electrosurgical device 112, FIG. 9B shows a perspective view of a distal end 926B of the shaft 126 of the electrosurgical device 112, FIG. 9C shows a side view of the distal end 926B of the shaft 126, FIG. 9D shows a cross-sectional view of the electrosurgical device 112 through a center axis shown in FIG. 9A, and FIG. 9E shows an exploded view of the electrosurgical device 112.

As shown in FIG. 9A, the electrosurgical device 112 includes the housing 124 defining the interior bore 125, the shaft 126 telescopically moveable in the interior bore 125 of the housing 124, and the electrosurgical electrode 128 coupled to the shaft 126. The shaft 126 has a center axis 968 extending from a proximal end of the shaft 126 to the distal end 926B of the shaft 126. Although the shaft 126 is telescopically moveable relative to the housing 124 in FIGS. 9A-9C, the shaft 126 can be fixedly coupled to the housing 124 such that the shaft 126 is not moveable relative to the housing 124 in other examples.

As shown in FIGS. 9B-9C, the shaft 126 includes a shaft wall 970 having an inner surface 970A and an outer surface 970B. The inner surface 970A of the shaft wall 970 defines the smoke evacuation channel 148 that extends from the distal end 926B of the shaft 126 to the proximal end of the shaft 126. As described above, the smoke evacuation channel 148 can provide the first portion of the smoke flow path along which surgical smoke flows as the surgical smoke is evacuated from a surgical site by the electrosurgical device 112.

For instance, in an example shown in FIG. 9C, the smoke evacuation channel 148 of the shaft 126 can define the first portion of the smoke flow path, and the interior bore 125 of the housing 124 can define the second portion of a smoke flow path as described above with respect to FIG. 2. In this example, the smoke received from the surgical site into the smoke evacuation channel 148 of the shaft 126 can flow proximally along the smoke evacuation channel 148 to the interior bore 125 of the housing 124. In the interior bore 125 of the housing 124, the smoke can further flow to the smoke tube 150 (shown in FIG. 1) that is coupled to a proximal end of the housing 124 and configured to convey the smoke from the housing 124 to the suction pump 146 (shown in FIG. 1).

In another example, the smoke evacuation channel 148 of the shaft 126 can define the first portion of the smoke flow path, and the smoke evacuation chamber 152 of the housing 124 can define the second portion of the smoke flow path as described above with respect to FIG. 3. In this example, as described above, the smoke can be routed through the smoke evacuation chamber 152 (shown in FIGS. 1 and 3), which is separate from the interior bore 125, to the smoke tube 150 at the proximal end of the housing 124. This can beneficially help to mitigate exposing one or more components of the electrosurgical device 112 to the surgical smoke in the housing 124. In some implementations, providing a separate smoke evacuation chamber 152 can additionally or alternatively help to improve the flow of surgical smoke by reducing (or eliminating) obstacles and impediments to gas flows along the second portion of the flow path.

As noted above, the electrosurgical electrode 128 is coupled to the shaft 126. As shown in FIGS. 9A and 9C-9E, a distal portion of the electrosurgical electrode 128 extends distally from the shaft 126, and the distal portion of the electrosurgical electrode 128 extends inwardly from a periphery of the shaft 126 to the center axis 968 of the shaft 126. The inwardly extending shape of the distal portion of the electrosurgical electrode 128 can help to provide greater flexibility in positioning and arranging the smoke evacuation channel 148 and/or an illumination feature (e.g., the light source 140, the optical waveguide 142, and/or the optical fibers 770) at the distal end 926B of the shaft 126.

In FIGS. 9A-9E, the electrosurgical electrode 128 includes (i) a first electrode portion 928A coupled to the periphery of the shaft 126 and extending along a direction that is parallel to the center axis 968, (ii) a second electrode portion 928B extending from the first electrode portion 928A to the center axis 968, and (iii) a third electrode portion 928C extending distally from the second electrode portion 928B and along the center axis 968 of the shaft 926. The electrosurgical electrode 128 can also include a first bend 928D between the first electrode portion 928A and the second electrode portion 928B, and a second bend 928E between the second electrode portion 928B and the third electrode portion 928C.

In an example, an angle between the first electrode portion 928A and the second electrode portion 928B is less than approximately 90 degrees. This can help to improve the flow of surgical smoke into the smoke evacuation channel 148 relative to an alternative implementation in which the angle between the first electrode portion 928A and the second electrode portion 928 is 90 degrees.

In operation, the surgical smoke can flow along a smoke flow path 988 shown in FIG. 9D. For instance, as shown in FIG. 9D, the surgical smoke can flow (i) along the second electrode portion 928B to enter the smoke evacuation channel 148 of the shaft 126, (ii) from the smoke evacuation channel 148 to the interior bore 125 of the housing 124, and (iii) from the interior bore 125 of the housing 124 to the smoke tube 150 at the proximal end of the housing 124.

As shown in FIGS. 9C and 9E, the shaft 126 can include (i) a first shaft portion 926A that extends between the proximal end and the distal end, and (ii) a second shaft portion 990B that extends between the proximal end and the distal end. As shown in FIG. 9C, the smoke evacuation channel 148 can be defined between the first shaft portion 990A and the second shaft portion 990B. In this example, the electrosurgical electrode 128 is coupled to the second shaft portion 990B. Although FIGS. 9A-9E show the shaft 126 including the first shaft portion 990A and the second shaft portion 990B, which can be coupled to each other, the shaft 126 can be a single-part, monolithic structure that defines the smoke evacuation channel 148 in other examples.

As shown in FIG. 9E, the electrosurgical device 112 can also include the electrical components that facilitate supplying the electrosurgical energy, which the electrosurgical device 112 receives from the electrosurgical generator 110, to the electrosurgical electrode 128. For example, as described above with respect to FIG. 1, the electrosurgical device 112 shown in FIG. 9E can include the printed circuit board 132, the housing conductor 134, and the conductive lead(s) 136 to form a circuit for conducting the electrosurgical energy from the power cord 122 to the electrosurgical electrode 128. In FIG. 9E, the housing conductor 134 is in the form of a conductive channel on an interior surface of the housing 124, and the conductive lead 136 is in the form of a conductive track that extends along the inner surface 970A of the shaft 126 with a portion of the conductive lead 136 being at the outer surface 970B of the shaft 126 at the proximal end of the shaft 126. In this arrangement, a distal end of the conductive lead 136 can electrically couple to the electrosurgical electrode 128 and a proximal end of the conductive lead 136 can electrically couple to the housing conductor 134 as the shaft 126 telescopically moves relative to the housing 124.

As noted above, the electrosurgical device 112 can include an illumination feature at the distal end 926B of the shaft 126. For example, as described above, the electrosurgical device 112 can include an illumination feature selected from a group consisting of one or more light sources, one or more optical fibers, and one or more optical waveguides. In the example shown in FIGS. 9B-9C, the electrosurgical device 112 includes the optical waveguide 142 extending through a passage 992 in the first shaft portion 990A. However, in another example, the electrosurgical device 112 can include the light source 140 at the distal end 926B of the shaft 126 and/or one or more optical fibers (e.g., the optical fibers 776) at the distal end 926B of the shaft 126.

Figure 10E:
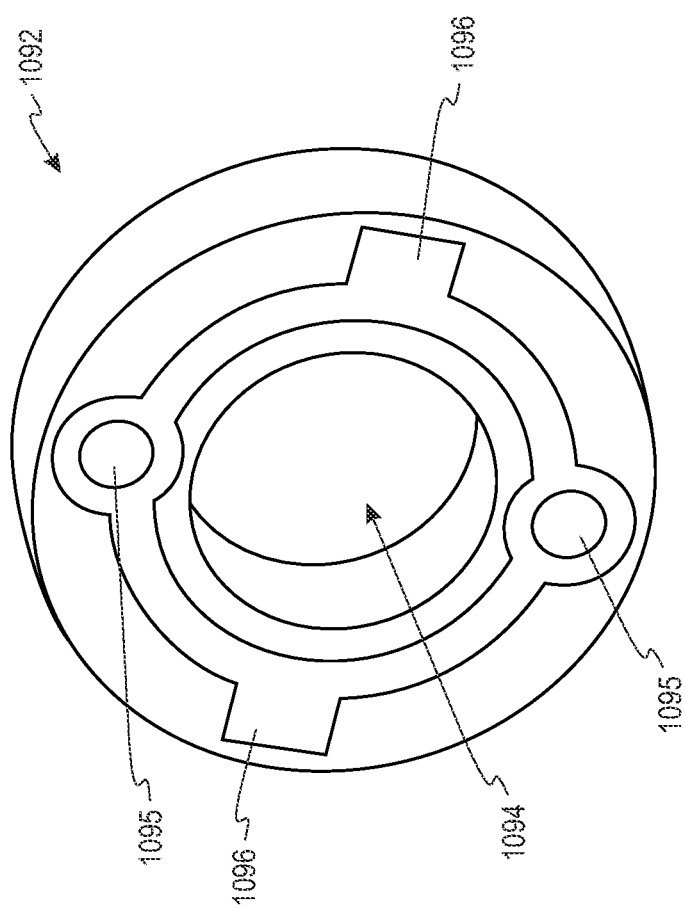
FIG. 10E depicts a light-emitting diode printed circuit board of the electrosurgical device shown in FIG. 10A, according to an example.
Figure 10D:
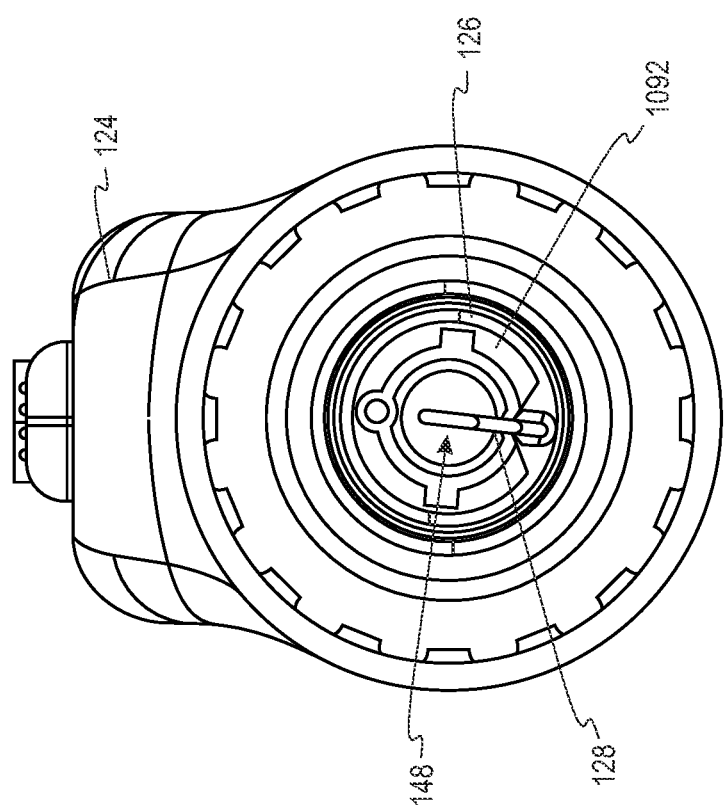
FIG. 10D depicts another side view of a distal end of the shaft of the electrosurgical device shown in FIG. 10B, according to an example.

FIGS. 10A-10E depicts an implementation of the electrosurgical device 112 in which the electrosurgical electrode 128 extends inwardly from a periphery of the shaft 126 to the center axis of the shaft 126 according to another example. In particular, FIG. 10A depicts a perspective view of the electrosurgical device 112, FIG. 10B depicts a perspective view of a distal end of the shaft 126 of the electrosurgical device 112 shown in FIG. 10A, FIG. 10C shows a side view of a distal end of the shaft 126 of the electrosurgical device 112 shown in FIG. 10A, FIG. 10D shows another side view of a distal end of the shaft 126 of the electrosurgical device 112 shown in FIG. 10A, and FIG. 10E shows a ring structure of the electrosurgical device 112 shown in FIG. 10A.

As shown in FIGS. 10A-10D, the electrosurgical device 112 includes the housing 124 defining the interior bore 125, the shaft 126 telescopically moveable in the interior bore 125 of the housing 124, and the electrosurgical electrode 128 coupled to the shaft 126. The shaft 126 has a center axis 1068 extending from a proximal end of the shaft 126 to the distal end 1026B of the shaft 126. Although the shaft 126 is telescopically moveable relative to the housing 124 in FIGS. 10A-10-D, the shaft 126 can be fixedly coupled to the housing 124 such that the shaft 126 is not moveable relative to the housing 124 in other examples.

In FIGS. 10A-10D, a distal portion of the electrosurgical electrode 128 extends distally from the shaft 126, and the distal portion of the electrosurgical electrode 128 extends inwardly from a periphery of the shaft 126 to the center axis 1068 of the shaft 126. The inwardly extending shape of the distal portion of the electrosurgical electrode 128 can help to provide greater flexibility in positioning and arranging the smoke evacuation channel 148 and/or an illumination feature (e.g., a light source 140) at the distal end 1026B of the shaft 126.

As shown in FIGS. 10D-10E, the electrosurgical device 112 can include a light-emitting diode printed circuit board (LED PCB) 1092 in the smoke evacuation channel 148 of the shaft 126. The LED PCB 1092 can include an aperture 1094 having a diameter that is smaller than a diameter of the smoke evacuation channel 148. The aperture 1094 can allow for smoke to pass through the LED PCB 1092 while evacuating smoke from the surgical site.

Figure 11:
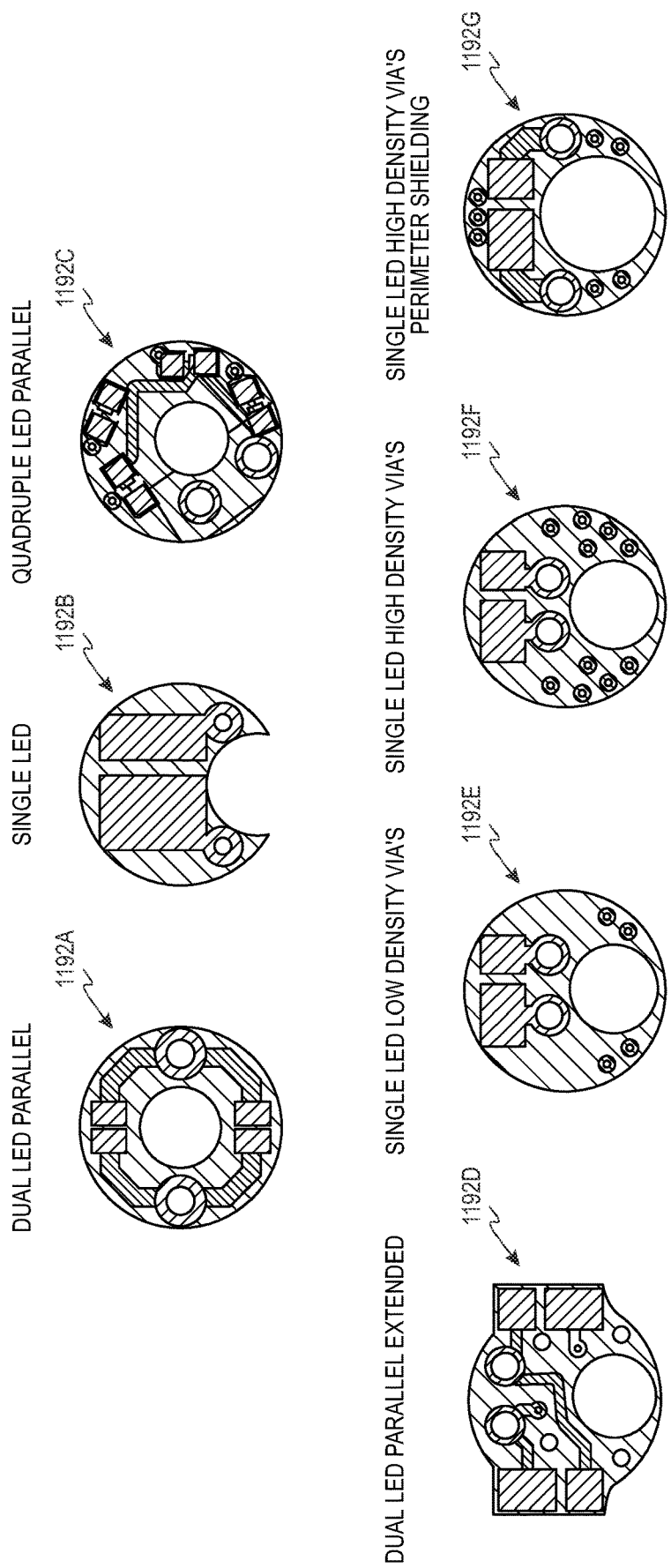
FIG. 11 depicts light-emitting diode printed circuit boards for the electrosurgical device shown in FIG. 10A, according to examples.

Additionally, as shown in FIGS. 10D-10E, the LED PCB 1092 can also include one or more electrical contacts 1095 electrically coupled to one or more LEDs 1096. The one or more electrical contacts 1095 can also couple to the conductive lead(s) 136 (shown in FIG. 1). In this way, the conductive lead(s) 136 can supply electrical power to the LEDs 1096 via the one or more electrical contacts 1095. In some examples, LED PCB 1092 can be plated to help reduce RF interference to the one or more LEDs 1096. FIG. 11 depicts a plurality of example LED PCBs 1192A-1192G that can be used with the electrosurgical device 112 shown in FIGS. 10A-10E according to examples.

Figure 10F:
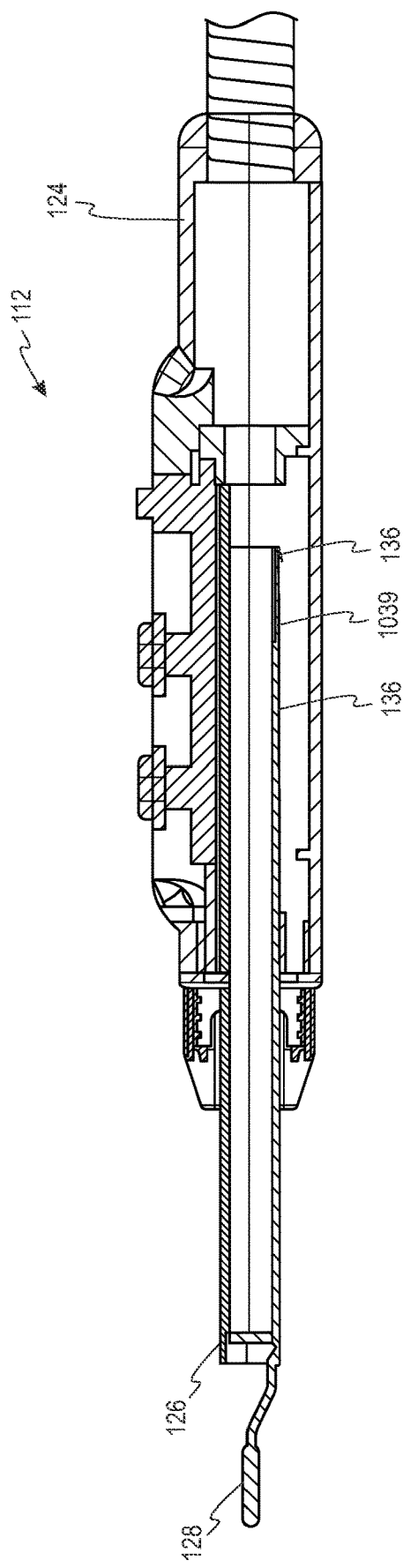
FIG. 10F depicts a cross-sectional view of the electrosurgical device shown in FIG. 10A, according to an example.

FIG. 10F shows a cross-sectional view of the electrosurgical device 112 through the longitudinal axis 1068, according to an example. As shown in FIG. 10F, the electrosurgical electrode 128 is integrally formed as a single-piece, monolithic structure with the conductive lead 136. In an example, the conductive lead 136 can have a semi-circle shape that corresponds to a circular shape of the inner surface of the shaft 126. The conductive lead 136 extends proximally from the electrosurgical electrode 128 to a conductive spring 1039. The conductive spring 1039 can extend around and/or through the shaft wall of the shaft 126 to electrically couple conductive lead 136 (and the electrosurgical electrode 128) to the housing conductor 134 of the housing 124. In this way, the conductive spring 1039 can provide for maintaining an electrical coupling between the conductive lead 136 and the housing conductor 134 in all axial positions of the shaft 126 relative to the housing 124.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. An electrosurgical device, comprising:
    a housing defining an interior bore;
    a shaft telescopically moveable in the interior bore of the housing, wherein the shaft comprises:
        an optical waveguide at a distal end of the shaft, and
        a smoke evacuation channel circumferentially surrounding the optical waveguide at the distal end of the shaft; and
    an electrosurgical electrode coupled to the shaft.

2. The electrosurgical device of claim 1, wherein the smoke evacuation channel and the optical waveguide are coaxial.

3. The electrosurgical device of claim 1, further comprising a plurality of standoffs separating an outer tube of the smoke evacuation channel from the optical waveguide.

4. The electrosurgical device of claim 1, wherein the smoke evacuation channel of the shaft defines a first portion of a smoke flow path, and wherein the interior bore of the housing defines a second portion of the smoke flow path.

5. The electrosurgical device of claim 4, further comprising a smoke tube coupled to a proximal end of the housing and configured to convey smoke from the housing to a suction pump.

6. The electrosurgical device of claim 1, wherein the housing comprises an interior wall separating the interior bore from a smoke evacuation chamber in the housing, wherein the smoke evacuation channel of the shaft is in fluid communication with the smoke evacuation chamber of the housing, wherein the smoke evacuation channel of the shaft defines a first portion of a smoke flow path, and wherein the smoke evacuation chamber of the housing defines a second portion of the smoke flow path.

7. The electrosurgical device of claim 6, wherein a proximal portion of the smoke evacuation channel comprises at least one aperture,
wherein the interior wall of the housing comprises at least one slot, and
wherein the at least one aperture of the smoke evacuation channel is aligned with the at least one slot of the interior wall of the housing such that wherein the smoke evacuation channel of the shaft is in fluid communication with the smoke evacuation chamber of the housing.

8. The electrosurgical device of claim 7, wherein the at least one aperture comprises a plurality of apertures and the at least one slot comprises a plurality of slots, wherein each aperture is aligned with a respective one of the plurality of slots, wherein the shaft is rotatable relative to the housing, and wherein the plurality of apertures and the plurality of slots are arranged around a circumference of the shaft such that fluid communication between the smoke evacuation channel and the smoke evacuation chamber is maintained when the shaft is rotated relative to the housing.

9. The electrosurgical device of claim 7, wherein the at least one aperture is axially movable along the at least one slot when the shaft telescopically moves relative to the housing.

10. The electrosurgical device of claim 6, further comprising a printed circuit board fixedly coupled to the housing in the interior bore,
wherein the printed circuit board comprises a plurality of switches that are operable to control a supply of electrosurgical energy from an electrosurgical generator to the electrosurgical electrode.

11. The electrosurgical device of claim 1, wherein the shaft is rotatable about an axis of rotation that is parallel to a longitudinal axis of the electrosurgical device.

12. The electrosurgical device of claim 1, wherein the electrosurgical electrode is rotatable relative to the shaft.

13. The electrosurgical device of claim 1, further comprising a light source optically coupled to the optical waveguide.

14. The electrosurgical device of claim 13, wherein the light source is coupled to the shaft such that the light source is telescopically movable with the shaft relative to the housing.

15. The electrosurgical device of claim 13, wherein the light source is in the interior bore of the housing.

16. The electrosurgical device of claim 13, wherein the light source is coupled to an exterior surface of the housing.

17. The electrosurgical device of claim 1, wherein the electrosurgical electrode extends from a central portion of the optical waveguide, and wherein the optical waveguide extends entirely around the electrosurgical electrode.

18. The electrosurgical device of claim 17, wherein the electrosurgical electrode extends from a central portion of the optical waveguide, and wherein the optical waveguide does not extend entirely around the electrosurgical electrode at the distal end of the shaft.

19. A method, comprising:
providing the electrosurgical device of claim 1;
supplying electrosurgical energy to the electrosurgical electrode; and
applying suction to the smoke evacuation channel.

20. The method of claim 19, wherein applying the suction to the smoke evacuation channel is performed while supplying the electrosurgical energy to the electrosurgical electrode.

* * * * *